(12) United States Patent
Hammond et al.

(10) Patent No.: US 8,222,359 B2
(45) Date of Patent: Jul. 17, 2012

(54) POLY(PROPARGYL-L-GLUTAMATE) AND DERIVATIVES THEREOF

(75) Inventors: Paula T. Hammond, Newton, MA (US); Amanda C. Engler, Cambridge, MA (US); Hyung-il Lee, Ulsan (KR)

(73) Assignee: Massachusetts Institute of Technology, Cambridge, MA (US)

( * ) Notice: Subject to any disclaimer, the term of this patent is extended or adjusted under 35 U.S.C. 154(b) by 269 days.

(21) Appl. No.: 12/607,592

(22) Filed: Oct. 28, 2009

(65) Prior Publication Data

US 2011/0097419 A1   Apr. 28, 2011

(51) Int. Cl.
C08F 126/06 (2006.01)
C07D 249/04 (2006.01)

(52) U.S. Cl. ...................................... 526/261; 548/227

(58) Field of Classification Search .................. None
See application file for complete search history.

(56) References Cited

U.S. PATENT DOCUMENTS

| 3,285,953 A | 11/1966 | Wasserman et al. |
| 2007/0244265 A1 | 10/2007 | Matyjaszewski et al. |
| 2008/0188638 A1 | 8/2008 | Breitenkamp et al. |

OTHER PUBLICATIONS

Engler, AC et al., Highly efficient "grafting onto" a polypeptide backbone using click chemistry. Angewandte Chemie, Intl. Ed., 48(49) 9334-8 (2009).
He, X et al., Synthesis of water-soluble ABC triblock copolymers containing polypeptide segments. Reactive and Functional Polymers 69(9):666-72 (2009).
Sanda, F et al., Helical polymer carrying helical grafts form peptide-based acetylene macromonomers: synthesis. Macromolecular Bioscience 4(6):570-4 (2004).
International Search Report for PCT/US2010/054264, dated Jul. 26, 2011.
Belshaw, P. J. et al., "Chlorotrimethylsilane Mediated Formation of ω—Allyl Esters of Aspartic Acid and Glutamin Acids," *Synthetic Communications* 20(20): 3157-3160 (1990).
Daly, W. H. et al., "The Preparation of N-Carboxyanhydrides of α-Amino Acids Using Bis(trichloromethyl)carbonate," *Tetrahedron Letters* 29(46):5859-5862 (1988).
Deming, T. J., "Facile Synthesis of Block Copolypeptides of Defined Architecture," *Nature* 390: 386-389 (1997).
Deming, T. J. "Synthetic Polypeptides for Biomedical Applications," *Prog. Polym. Sci.* 32: 858-875 (2007).
Gao, H. et al., "Synthesis of Molecular Brushes by "Grafting onto" Method: Combination of ATRP and Click Reactions," *J. Am. Chem. Soc.* 129: 6633-6639 (2007).
Kolb, H. C. et al., "Click Chemistry: Diverse Chemical Function from a Few Good Reactions," *Angew. Chem. Int. Ed.* 40: 2004-2021 (2001).
Lu, H. et al., "Hexamethyldisilazane-Mediated Controlled Polymerization of α-Amino Acid N-Carboxyanhydrides," *J. Am. Chem. Soc.* 129(46): 14114-14115 (2007).
Lu, H. et al.,"N-Trimethylsilyl Amines for Controlled ring-Opening Polymerization of Amino Acid N-Carboxyanhydrides and Facile End Group Functionalization of Polypeptides," Supporting Information for *J. Am. Chem. Soc.* 129(46): 14114-14115 (2007), S1-S8.
Osada, K. et al., "Drug and Gene Delivery Based on Supramolecular Assembly of PEG-Polypeptide Hybrid Block Copolymers," *Adv. Polym. Sci.* 202:113-153 (2006).
Pickel, D. L., et al., "A Mechanistic Study of -(Amino acid)-N-Carboxyanhydride Polymerization: Comparing Initiation and Termination Events in High-Vacuum and Traditional Polymerization Techniques," *Macromolecules,* 42(20): 7781-7788 (2009).
Poché, D. S. et al., An Unconventional Method for Purifying the N-Carboxyanhydride Derivatives of γ—Alkyl-L-Glutamates, *Synthetic Communications* 29(5): 843-854 (1999).
Tian L. et al., "Comb-dendritic Block Copolymers as Tree-shaped Macromolecule Amphiphiles for Nanoparticle Self-assembly," *Chemistry of Materials* 18: 3976-3984 (2006).
Tian L. et al., "Vesicular Self-assembly of Comb-dendritic Block Copolymers," *Chem. Commun.* 33: 3489-3491 (2006).

*Primary Examiner* — Kamal Saeed
(74) *Attorney, Agent, or Firm* — Alan W. Steele; Foley Hoag LLP

(57) ABSTRACT

A process of the present invention is directed toward conducting highly selective, high yield post-polymerization reactions on polypeptides to prepare functionalized polypeptides. In certain embodiments, the polypeptides can be prepared by ring opening polymerization of N-carboxyanhydrides. In certain embodiments, the post-polymerization reaction is a "click chemistry" reaction. In certain embodiment, the "click chemistry" reaction is a triazole-forming reaction involving an alkyne on the polypeptide and an azide.

11 Claims, 15 Drawing Sheets

[A]

[B]

A

B

POLY(PROPARGYL-L-GLUTAMATE) AND DERIVATIVES THEREOF

BACKGROUND

Polymers with attached functional groups may be prepared directly by polymerization of functional monomers (i.e., monomers appended with the functional groups). However, some functional monomers may not be directly polymerized by any polymerization process or may not polymerize in the desired manner. In such case, post-polymerization modification, such as the "grafting onto" method, is necessary to prepare a desired polymer. For example, "click chemistry" has been used in a wide variety of polymer applications including functionalization of polymers with small molecules, formation of diblock polymers, formation of new dendrimers, formation of macromonomers, crosslinking of micelles, and the "grafting onto" method of forming molecular brushes (see, for example, U.S. Patent Application Publication No. 2007/0244265 to Matyjaszewski, which is the U.S. national stage of International Patent Application No. PCT/US05/07264, and which is hereby incorporated by reference in its entirety).

Synthetic polypeptides with attached functional groups have been used to prepare "tailored polypeptides." Tailored polypeptides have attracted significant interest for hybrid polymer drug and gene delivery systems, tissue engineering, and polypeptide adhesives. Synthetic polypeptides have several features that make them very attractive for biological applications including low toxicity, biodegradability, predictable structures, and well-controlled dimensions. Synthetic polypeptides have previously been synthesized using a well-studied N-carboxyanhydride (NCA) ring-opening polymerization (ROP) which utilizes a wide variety of monomers containing various functional groups. In particular, carboxylic acid (e.g., glutamate and aspartate) and amino (e.g., lysine) groups of the amino acids have been used to add chemical moieties such as pharmaceutical drugs and molecules that dictate hydrophobicity or pH responsiveness. However, functionalization of polypeptides synthesized by NCA ROP has several limitations. Because of the nature of the polymerization, the type of monomer that can be used is limited to NCAs with alkane end groups or NCAs where the functional group is protected. When creating polypeptides with functional carboxylic acid or amino groups, a three step process is often required: (1) polymerization with the protected functional group, (2) the deprotection of the functional group, and (3) the functionalization. In addition, if a high degree of functionalization is required, the added chemical moieties are limited to small molecules and low molecular weight oligomers. In addition, the addition of polymeric side chains using a "grafting onto" method at a high grafting density has not been attainable; in fact, the addition of polymeric side chains using a "grafting onto" method at a high grafting density (i.e., above 50%) has not been attainable.

SUMMARY

One aspect of the invention relates to N-carboxyanhydrides (NCA) substituted with a reactive functional group. Another aspect of the invention relates to the use of N-carboxyanhydrides substituted with a reactive functional group in polymerization reactions to form synthetic polypeptides. Certain aspects of the invention relate to high yield post polymerization reactions of the reactive functional groups of said polypeptides. In certain embodiments, the polypeptides are prepared by a ring opening polymerization. In certain embodiments, the highly selective, high yield post polymerization reaction is a "click chemistry" reaction of the reactive functional groups attached to the polypeptide. In certain embodiments, almost perfect grafting densities (e.g., greater than about 95%) are obtained. Additional aspects, embodiments, and advantages of the invention are discussed below in detail.

DETAILED DESCRIPTION

Figure 1:
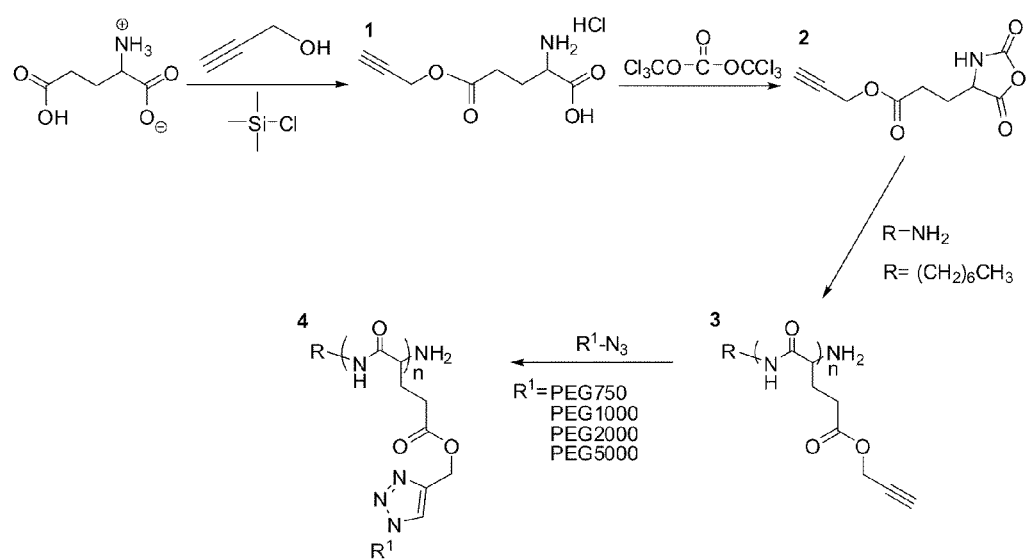
FIG. 1 depicts synthetic steps in an exemplary approach to the preparation of poly(propargyl-L-glutamate) (PPLG) and its derivatives.

One aspect of the invention relates to a synthetic method to form highly functionalized, grafted polypeptides. For example, a N-carboxyanhydride (NCA) monomer of propargyl-L-glutamate and its polymer, PPLG, have been synthesized. This polymer provides a means of attaching a wide variety of molecules, varying in both size and hydrophobicity, to a polypeptide using a single step click reaction. The combination of NCA ring opening polymerization (ROP), and "click chemistry" provides a versatile synthetic approach to develop molecules which mimic the complex architecture of natural peptides. As described herein PEG chains with varying molecular weight from 750 Da to 5000 Da can be attached to the PPLG backbone at high grafting densities. For example, a grafting density of 95.8% was obtained at an alkyne/azide reaction ratio of 1/1, and a grafting density of 96.3-98.9% was obtained at reaction ratios of alkyne/azide of 1/2. The high efficiency achieved with PPLG is a result, at least in part, of the rigid α-helical structure of the polymer backbone which causes the alkyne terminated side chains to protrude outward from each repeat unit, thus increasing their accessibility for coupling.

Definitions

For convenience, certain terms employed in the specification, examples, and appended claims are collected here. All definitions, as defined and used herein, supersede dictionary definitions, definitions in documents incorporated by reference, and/or ordinary meanings of the defined terms.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e., six carbons or less). For example "lower alkyl" refers to an alkyl group containing 1-6 carbons, and "lower alkenyl" refers to an alkyenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing $4n+2$ electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 20, 1 to 15, or 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene," is art-recognized, and as used herein pertains to a bidentate moiety obtained by removing two hydrogen atoms of an alkyl group, as defined above.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, haloalkylsulfinyloxy, fluororalkylsulfinyloxy, alkenylsulfinyloxy, alkynylsulfinyloxy, alkoxysulfinyloxy, halo alkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "aryl," as used herein means a phenyl group, naphthyl or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, haloalkylsulfinyloxy, fluororalkylsulfinyloxy, alkenylsulfinyloxy, alkynylsulfinyloxy, alkoxysulfinyloxy, haloalkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluororalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluororalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluororalkylsulfonyloxy, alkenylsulfonyloxy, alkynylsulfonyloxy, haloalkoxysulfonyloxy, fluororalkoxysulfonyloxy, alkenyloxysulfonyloxy, alkynyloxysulfonyloxy, alkylsulfinyloxy, haloalkylsulfinyloxy, fluororalkylsulfinyloxy, alkenylsulfinyloxy, alkynylsulfinyloxy, alkoxysulfinyloxy, haloalkoxysulfinyloxy, fluororalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g., methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluororalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluororalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy" are likewise defined.

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" or "azide" as used herein means a —N$_3$ group.

The term "phosphinyl" or "phosphino" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkoxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

As used herein, the "main chain" of a polymer, or the "backbone" of the polymer, is the series of bonded atoms that together create the continuous chain of the molecule. As used herein, a "side chain" of a polymer is the series of bonded atoms which are pendent from the main chain of a polymer.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

The abbreviation "PEG" as used herein is known to those skilled in the art and refers to poly(ethylene) glycols (linear or branched). Shown below is a structure for a linear polyethylene glycol:

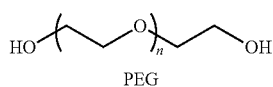

PEG

In the structure provided above n is a positive integer. In a batch of activated PEG different individual molecules will have a different values of n (i.e., the mixture is polydisperse); these mixtures are often characterized by an average molecular weight, which can be converted into an average value for n. If given a molecular weight, an approximate value of n can be calculated by dividing the molecular weight by 42 and subtracting 1.

The abbreviation "PPLG" as used herein refers to poly(γ-propargyl L-glutamate). Shown below is a structure for poly(γ-propargyl L-glutamate). In the structure provided below n is a positive integer.

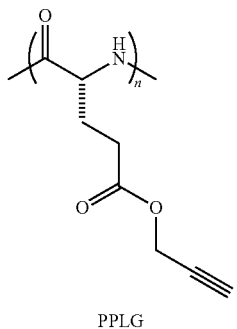

PPLG

Click Chemistry

As used herein, a "click chemistry" reaction is a reliable, high-yield, and selective reaction having a thermodynamic driving force of greater than or equal to 20 kcal/mol. Click chemistry reactions may be used for synthesis of molecules comprising heteroatom links. One of the most frequently used click chemistry reactions involves cycloaddition between azides and alkynyl/alkynes to form the linkage comprising a substituted or unsubstituted 1,2,3-triazole. Therefore, an embodiment of the process of the present invention comprises reacting a polymer comprising at least one acetylene bond with an azide to form a polymer comprising at least one triazole ring. In certain embodiments, the azide may be a functionalized azide.

Monomers

One aspect of the invention relates to a monomer represented by formula I:

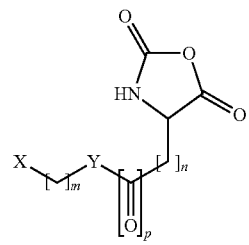

I or a tautomer, enantiomer or stereoisomer thereof;
wherein, independently for each occurrence,
X is alkynyl or azide;
m is 1-18 inclusive;
p is 0 or 1;
Y is O, N(H), N(alkyl), C(H)$_2$, C(H)(alkyl) or C(alkyl)$_2$; and
n is 1-10 inclusive.

In certain embodiments, the present invention relates to any one of the aforementioned monomers, wherein m is 1. In certain embodiments, the present invention relates to any one of the aforementioned monomers, wherein m is 2. In certain embodiments, the present invention relates to any one of the aforementioned monomers, wherein m is 3. In certain embodiments, the present invention relates to any one of the aforementioned monomers, wherein m is 4. In certain embodiments, the present invention relates to any one of the aforementioned monomers, wherein m is 5. In certain embodiments, the present invention relates to any one of the aforementioned monomers, wherein m is 6. In certain embodiments, the present invention relates to any one of the aforementioned monomers, wherein m is 7. In certain embodiments, the present invention relates to any one of the aforementioned monomers, wherein m is 8. In certain embodiments, the present invention relates to any one of the aforementioned monomers, wherein m is 9. In certain embodiments, the present invention relates to any one of the aforementioned monomers, wherein m is 10.

In certain embodiments, the present invention relates to any one of the aforementioned monomers, wherein p is 1. In certain embodiments, the present invention relates to any one of the aforementioned monomers, wherein p is 0.

In certain embodiments, the present invention relates to any one of the aforementioned monomers, wherein n is 1. In certain embodiments, the present invention relates to any one of the aforementioned monomers, wherein n is 2. In certain embodiments, the present invention relates to any one of the aforementioned monomers, wherein n is 3. In certain embodiments, the present invention relates to any one of the aforementioned monomers, wherein n is 4. In certain embodiments, the present invention relates to any one of the aforementioned monomers, wherein n is 5. In certain embodiments, the present invention relates to any one of the aforementioned monomers, wherein n is 6. In certain embodiments, the present invention relates to any one of the aforementioned monomers, wherein n is 7. In certain embodiments, the present invention relates to any one of the aforementioned monomers, wherein n is 8. In certain embodiments, the present invention relates to any one of the aforementioned monomers, wherein n is 9. In certain embodiments, the present invention relates to any one of the aforementioned monomers, wherein n is 10.

In certain embodiments, the present invention relates to any one of the aforementioned monomers, wherein Y is O. In certain embodiments, the present invention relates to any one of the aforementioned monomers, wherein Y is N(H). In certain embodiments, the present invention relates to any one of the aforementioned monomers, wherein Y is C(H)$_2$.

In certain embodiments, the present invention relates to any one of the aforementioned monomers, wherein X is C≡CH or C≡C(lower alkyl). In certain embodiments, the present invention relates to any one of the aforementioned monomers, wherein X is C≡CH. In certain embodiments, the present invention relates to any one of the aforementioned monomers, wherein X is N$_3$.

In certain embodiments, the present invention relates to any one of the aforementioned monomers, wherein m is 2; p is 1; and n is 2. In certain embodiments, the present invention relates to any one of the aforementioned monomers, wherein m is 2; p is 1; n is 2; and Y is O. In certain embodiments, the present invention relates to any one of the aforementioned monomers, wherein m is 2; p is 1; n is 2; Y is O; and X is C≡CH.

Certain monomers of the invention may contain one or more chiral centers, and exist in different optically active forms. When monomers of the invention contain one chiral center, the monomers exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric monomers may be separated by methods known to those skilled in the art, for example chromatography or crystallization and the individual enantiomers may be separated as described above. The present invention includes each diastereoisomer of monomers of the invention and mixtures thereof.

Certain monomers of the invention may exist in different tautomeric forms or as different geometric isomers, and the present invention includes each tautomer and/or geometric isomer of monomers of the invention and mixtures thereof.

Certain monomers of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of monomers of the invention and mixtures thereof.

Polymers

The monomers described above can be polymerized alone or with other NCAs. For example, the monomers can be polymerized with other amino acid NCAs (such as the N-carboxyanhydrides of Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val)) to form copolymer.

One aspect of the invention relates to a polymer comprising a plurality of subunits represented by formula II:

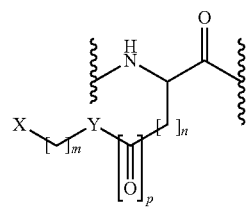

II or a tautomer, enantiomer or stereoisomer thereof;
wherein, independently for each occurrence,
  X is alkynyl or azide;
  m is 1-18;
  p is 0 or 1;
  Y is O, N(H), N(alkyl), C(H)$_2$, C(H)(alkyl) or C(alkyl)$_2$; and
  n is 1-10.

In certain embodiments, the present invention relates to any one of the aforementioned polymers, wherein the polymer consists essentially of a plurality of subunits represented by formula II. In certain embodiments, the present invention relates to any one of the aforementioned polymers, wherein the polymer consists essentially of between about 5 and about 300 subunits of formula II. A polymer which is noted as "consisting essentially of" a number of subunits has less than about 10 other subunits and may include one of the terminal subunits discussed below. In certain embodiments, the present invention relates to any one of the aforementioned polymers, wherein the polymer consists essentially of between about 5 and about 50 subunits of formula II. In certain embodiments, the present invention relates to any one of the aforementioned polymers, wherein the polymer consists essentially of between about 50 and about 100 subunits of formula II. In certain embodiments, the present invention relates to any one of the aforementioned polymers, wherein the polymer consists essentially of between about 100 and about 150 subunits of formula II. In certain embodiments, the present invention relates to any one of the aforementioned polymers, wherein the polymer consists essentially of between about 150 and about 200 subunits of formula II.

In certain embodiments, the present invention relates to any one of the aforementioned polymers, wherein m is 1. In certain embodiments, the present invention relates to any one of the aforementioned polymers, wherein m is 2. In certain embodiments, the present invention relates to any one of the aforementioned polymers, wherein m is 3. In certain embodiments, the present invention relates to any one of the aforementioned polymers, wherein m is 4. In certain embodiments, the present invention relates to any one of the aforementioned polymers, wherein m is 5. In certain embodiments, the present invention relates to any one of the aforementioned polymers, wherein m is 6. In certain embodiments, the present invention relates to any one of the aforementioned polymers, wherein m is 7. In certain embodiments, the present invention relates to any one of the aforementioned polymers, wherein m is 8. In certain embodiments, the present invention relates to any one of the aforementioned polymers, wherein m is 9. In certain embodiments, the present invention relates to any one of the aforementioned polymers, wherein m is 10.

In certain embodiments, the present invention relates to any one of the aforementioned polymers, wherein p is 1. In certain embodiments, the present invention relates to any one of the aforementioned polymers, wherein p is 0.

In certain embodiments, the present invention relates to any one of the aforementioned polymers, wherein n is 1. In certain embodiments, the present invention relates to any one of the aforementioned polymers, wherein n is 2. In certain embodiments, the present invention relates to any one of the aforementioned polymers, wherein n is 3. In certain embodiments, the present invention relates to any one of the aforementioned polymers, wherein n is 4. In certain embodiments, the present invention relates to any one of the aforementioned polymers, wherein n is 5. In certain embodiments, the present invention relates to any one of the aforementioned polymers, wherein n is 6. In certain embodiments, the present invention relates to any one of the aforementioned polymers, wherein n is 7. In certain embodiments, the present invention relates to any one of the aforementioned polymers, wherein n is 8. In certain embodiments, the present invention relates to any one of the aforementioned polymers, wherein n is 9. In certain embodiments, the present invention relates to any one of the aforementioned polymers, wherein n is 10.

In certain embodiments, the present invention relates to any one of the aforementioned polymers, wherein Y is O. In certain embodiments, the present invention relates to any one of the aforementioned polymers, wherein Y is N(H). In certain embodiments, the present invention relates to any one of the aforementioned polymers, wherein Y is $C(H)_2$.

In certain embodiments, the present invention relates to any one of the aforementioned polymers, wherein X is C≡CH or C≡C(lower alkyl). In certain embodiments, the present invention relates to any one of the aforementioned polymers, wherein X is C≡CH. In certain embodiments, the present invention relates to any one of the aforementioned polymers, wherein X is azide.

In certain embodiments, the present invention relates to any one of the aforementioned polymers, wherein m is 2; p is 1; and n is 2. In certain embodiments, the present invention relates to any one of the aforementioned polymers, wherein m is 2; p is 1; n is 2; and Y is O. In certain embodiments, the present invention relates to any one of the aforementioned polymers, wherein m is 2; p is 1; n is 2; Y is O; and X is C≡CH.

In certain embodiments, the present invention relates to any one of the aforementioned polymers, wherein the polymer further comprises one terminal subunit represented by formula III:

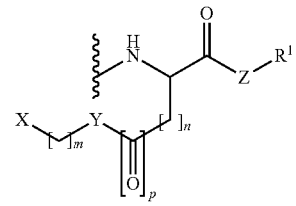

or a tautomer, enantiomer or stereoisomer thereof;
wherein, independently for each occurrence,
Z is N(H) or O;
$R^1$ is hydrogen, alkyl,

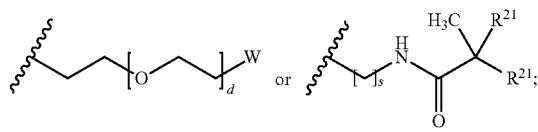

d is about 10 to about 300;
s is 1-5;
W is hydroxy, a protected hydroxy, alkoxy, aryloxy, heteroaryloxy, aralkoxy, heteroaralkoxy, amino, or a protected amino;
$R^{21}$ is

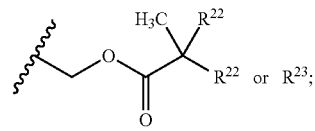

$R^{22}$ is

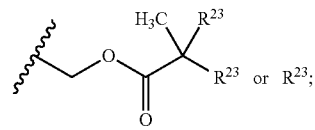

$R^{23}$ is

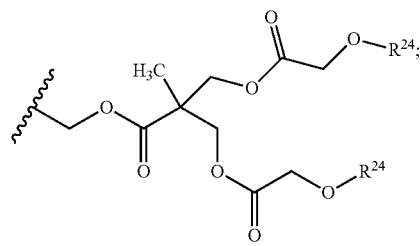

and
R²⁴ is

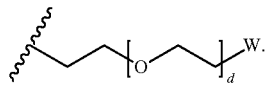

In certain embodiments, the present invention relates to any one of the aforementioned polymers, wherein Z is N(H). In certain embodiments, the present invention relates to any one of the aforementioned polymers, wherein $R^1$ is hydrogen. In certain embodiments, the present invention relates to any one of the aforementioned polymers, wherein $R^1$ is alkyl. In certain embodiments, the present invention relates to any one of the aforementioned polymers, wherein Z is N(H); and $R^1$ is heptyl.

In certain embodiments, the present invention relates to any one of the aforementioned polymers, wherein Z is O. In certain embodiments, the present invention relates to any one of the aforementioned polymers, wherein $R^1$ is hydrogen. In certain embodiments, the present invention relates to any one of the aforementioned polymers, wherein $R^1$ is alkyl. In certain embodiments, the present invention relates to any one of the aforementioned polymers, wherein Z is O; and $R^1$ is heptyl.

In certain embodiments, the present invention relates to any one of the aforementioned polymers, wherein $R^1$ is

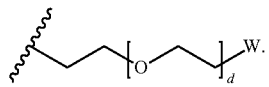

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150.

In certain embodiments, the present invention relates to any one of the aforementioned polymers, wherein W is a protected hydroxy. In certain embodiments, the present invention relates to any one of the aforementioned polymers, wherein W is alkoxy. For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O) CH₃). In certain embodiments, the present invention relates to any one of the aforementioned polymers, wherein W is methoxy. In certain embodiments, the present invention relates to any one of the aforementioned polymers, wherein W is acyloxy. In certain embodiments, the present invention relates to any one of the aforementioned polymers, wherein W is alkylcarbonyloxy.

In certain embodiments, the present invention relates to any one of the aforementioned polymers, wherein W is a protected amino, for example, as: a methyl amide (—NHC(=O)CH₃); a benzyloxy amide (—NHC(=O)OCH₂C₆H₅NHCbz); as a t-butoxy amide (—NHC=(=O)OC(CH₃)₃,—NHBoc); a 2-biphenyl-2-propoxy amide (—NHC(=O)OC(CH₃)₂C₆H₄C₆H₅NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), or as a 2-(phenylsulfonyl)ethyloxy amide (—NHPsec).

In certain embodiments, the present invention relates to any one of the aforementioned polymers, wherein $R^1$ is

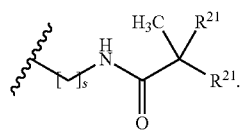

In certain embodiments, the present invention relates to any one of the aforementioned polymers, wherein Z is N(H); and $R^1$ is

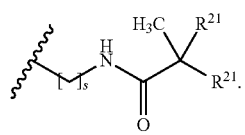

In certain embodiments, the present invention relates to any one of the aforementioned polymers, wherein s is 1. In certain embodiments, the present invention relates to any one of the aforementioned polymers, wherein s is 2. In certain embodiments, the present invention relates to any one of the aforementioned polymers, wherein s is 3. In certain embodiments, the present invention relates to any one of the aforementioned polymers, wherein s is 4. In certain embodiments, the present invention relates to any one of the aforementioned polymers, wherein s is 5.

In certain embodiments, the present invention relates to any one of the aforementioned polymers, wherein $R^{21}$ is

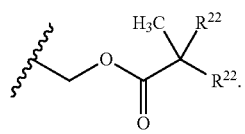

In certain embodiments, the present invention relates to any one of the aforementioned polymers, wherein $R^{22}$ is

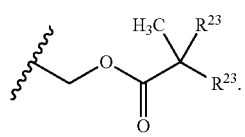

In certain embodiments, $R^1$ may be a dendrimer, such as those described in Tian L, Hammond P T, "Comb-dendritic block copolymers as tree-shaped macromolecule amphiphiles for nanoparticle self-assembly", *Chemistry of Materials* 2006, 18, 3976-3984; and Tian L, Nguyen P, Hammond P T, "Vesicular self-assembly of comb-dendritic block copolymers", *Chem. Commun.* 2006, 33, 3489-3491; both of which are hereby incorporated by reference.

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150.

In certain embodiments, the present invention relates to any one of the aforementioned polymers, wherein W is a protected hydroxy. In certain embodiments, the present invention relates to any one of the aforementioned polymers, wherein W is alkoxy. For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O) CH$_3$). In certain embodiments, the present invention relates to any one of the aforementioned polymers, wherein W is methoxy. In certain embodiments, the present invention relates to any one of the aforementioned polymers, wherein W is acyloxy. In certain embodiments, the present invention relates to any one of the aforementioned polymers, wherein W is alkylcarbonyloxy.

In certain embodiments, the present invention relates to any one of the aforementioned polymers, wherein W is a protected amino, for example, as: a methyl amide (—NHC (=O)CH$_3$); a benzyloxy amide (—NHC(=O) OCH$_2$C$_6$H$_5$NHCbz); as a t-butoxy amide (—NHC=(=O) OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), or as a 2-(phenylsulfonyl)ethyloxy amide (—NHPsec).

One aspect of the invention relates to a polymer comprising a plurality of subunits represented by formula IV:

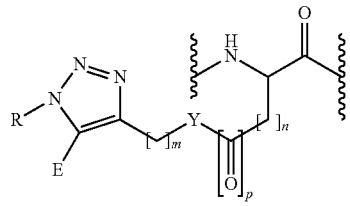

IV or a tautomer, enantiomer or stereoisomer thereof;

wherein, independently for each occurrence,

E is hydrogen or alkyl;

R is alkyl, haloalkyl, cycloalkyl, (cycloalkyl)alkyl, heterocyclyl, (heterocyclyl)alkyl, aryl, aralkyl, heteroaryl, heteroaralkyl, alkoxy,

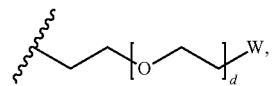

alkyloxycarbonylalkyl, carboxyalkyl, aminocarbonylalkyl, aminoalkyl,

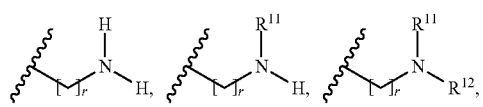

aminoalkylaminoalkyl, a polymer, polystyrene, polyethylene glycol, poly(methyl methyacrylate), a fluorescent dye or a radioactive dye;

d is about 10 to about 300;

W is hydroxy, a protected hydroxy, alkoxy, aryloxy, heteroaryloxy, aralkoxy, heteroaralkoxy, amino or a protected amino;

r is 1-10;

R$^1$ is alkyl, aminoalkyl or alkoxycarbonylaminoalkyl;

R$^{12}$ is alkyl, aminoalkyl or alkoxycarbonylaminoalkyl;

m is 1-20 inclusive;

p is 0 or 1;

Y is O, N(H), N(alkyl), C(H)$_2$, C(H)(alkyl) or C(alkyl)$_2$; and n is 1-10 inclusive.

In certain embodiments, the present invention relates to any one of the aforementioned polymers, wherein the polymer consists essentially of a plurality of subunits represented by formula IV. In certain embodiments, the present invention relates to any one of the aforementioned polymers, wherein the polymer consists essentially of between about 5 and about 300 subunits of formula IV. In certain embodiments, the present invention relates to any one of the aforementioned polymers, wherein the polymer consists essentially of between about 5 and about 50 subunits of formula IV. In certain embodiments, the present invention relates to any one of the aforementioned polymers, wherein the polymer consists essentially of between about 50 and about 100 subunits of formula IV. In certain embodiments, the present invention relates to any one of the aforementioned polymers, wherein the polymer consists essentially of between about 100 and about 150 subunits of formula IV. In certain embodiments, the present invention relates to any one of the aforementioned polymers, wherein the polymer consists essentially of between about 150 and about 200 subunits of formula IV.

In certain embodiments, the present invention relates to any one of the aforementioned polymers, wherein E is hydrogen. In certain embodiments, the present invention relates to any one of the aforementioned polymers, wherein E is alkyl.

In certain embodiments, the present invention relates to any one of the aforementioned polymers, wherein R is

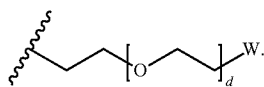

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150.

In certain embodiments, the present invention relates to any one of the aforementioned polymers, wherein W is hydroxy. In certain embodiments, the present invention relates to any one of the aforementioned polymers, wherein W is alkoxy. In certain embodiments, the present invention relates to any one of the aforementioned polymers, wherein W is methoxy.

In certain embodiments, the present invention relates to any one of the aforementioned polymers, wherein W is a protected hydroxy. In certain embodiments, the present invention relates to any one of the aforementioned polymers, wherein W is alkoxy. For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$). In certain embodiments, the present invention relates to any one of the aforementioned polymers, wherein W is methoxy. In certain embodiments, the present invention relates to any one of the aforementioned polymers, wherein W is acyloxy. In certain embodiments, the present invention relates to any one of the aforementioned polymers, wherein W is alkylcarbonyloxy.

In certain embodiments, the present invention relates to any one of the aforementioned polymers, wherein W is a protected amino, for example, as: a methyl amide (—NHC(=O)CH$_3$); a benzyloxy amide (—NHC(=O)OCH$_2$C$_6$H$_5$NHCbz); as a t-butoxy amide (—NHC(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), or as a 2-(phenylsulfonyl)ethyloxy amide (—NHPsec).

In certain embodiments, the present invention relates to any one of the aforementioned polymers, wherein R is benzyl,

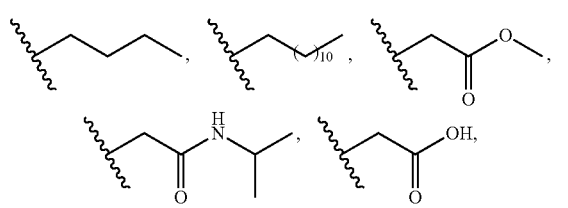

-continued

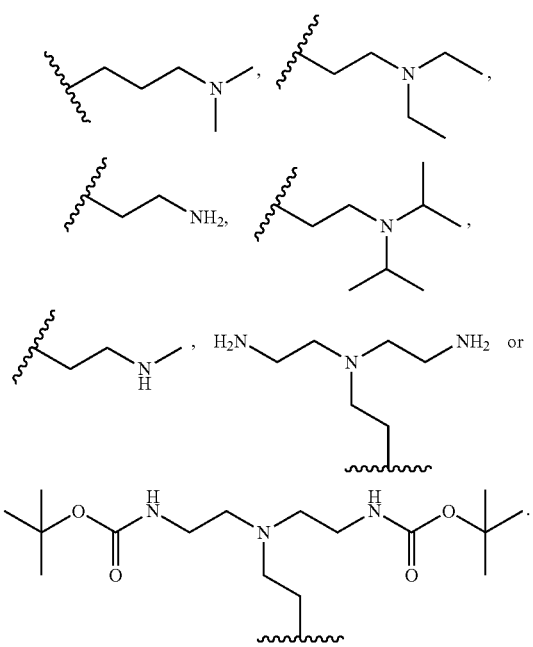

In certain embodiments, the present invention relates to any one of the aforementioned polymers, wherein R is

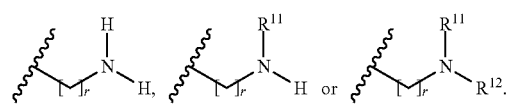

In certain embodiments, the present invention relates to any one of the aforementioned polymers, wherein at least one instance of R is

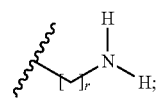

at least one instance of R is

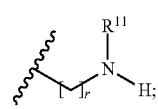

and at least one instance of R is

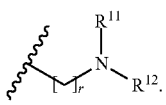

In certain embodiments, the present invention relates to any one of the aforementioned polymers, wherein at least one instance of R is

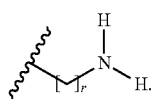

In certain embodiments, the present invention relates to any one of the aforementioned polymers, wherein R is

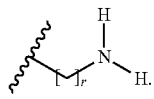

In certain embodiments, the present invention relates to any one of the aforementioned polymers, wherein at least one instance of R is

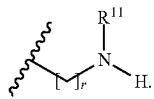

In certain embodiments, the present invention relates to any one of the aforementioned polymers, wherein R is

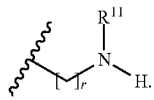

In certain embodiments, the present invention relates to any one of the aforementioned polymers, wherein at least one instance of R is

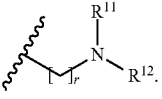

In certain embodiments, the present invention relates to any one of the aforementioned polymers, wherein R is

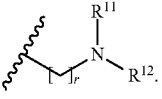

In certain embodiments, the present invention relates to any one of the aforementioned polymers, wherein R is

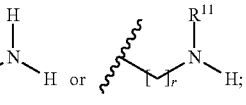

provided that at least one instance of R is

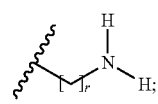

and at least one instance of R is

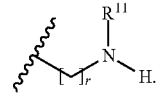

In certain embodiments, the present invention relates to any one of the aforementioned polymers, wherein R is

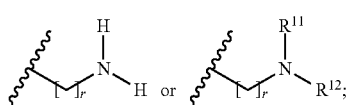

provided that at least one instance of R is

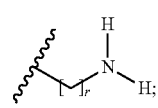

and at least one instance of R is

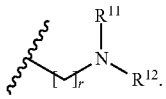

In certain embodiments, the present invention relates to any one of the aforementioned polymers, wherein R is

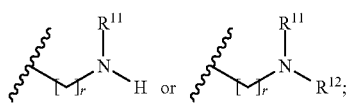

provided that at least one instance of R is

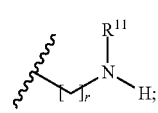

and at least one instance of R is

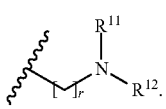

In certain embodiments, the present invention relates to any one of the aforementioned polymers, wherein $R^{11}$ is methyl. In certain embodiments, the present invention relates to any one of the aforementioned polymers, wherein $R^{11}$ is ethyl. In certain embodiments, the present invention relates to any one of the aforementioned polymers, wherein $R^{11}$ is isopropyl.

In certain embodiments, the present invention relates to any one of the aforementioned polymers, wherein $R^{12}$ is methyl. In certain embodiments, the present invention relates to any one of the aforementioned polymers, wherein $R^{12}$ is ethyl. In certain embodiments, the present invention relates to any one of the aforementioned polymers, wherein $R^{12}$ is isopropyl.

In certain embodiments, the present invention relates to any one of the aforementioned polymers, wherein r is 1-4. In certain embodiments, the present invention relates to any one of the aforementioned polymers, wherein r is 1. In certain embodiments, the present invention relates to any one of the aforementioned polymers, wherein r is 2. In certain embodiments, the present invention relates to any one of the aforementioned polymers, wherein r is 3. In certain embodiments, the present invention relates to any one of the aforementioned polymers, wherein r is 4.

In certain embodiments, the present invention relates to any one of the aforementioned polymers, wherein m is 1. In certain embodiments, the present invention relates to any one of the aforementioned polymers, wherein m is 2. In certain embodiments, the present invention relates to any one of the aforementioned polymers, wherein m is 3. In certain embodiments, the present invention relates to any one of the aforementioned polymers, wherein m is 4. In certain embodiments, the present invention relates to any one of the aforementioned polymers, wherein m is 5. In certain embodiments, the present invention relates to any one of the aforementioned polymers, wherein m is 6. In certain embodiments, the present invention relates to any one of the aforementioned polymers, wherein m is 7. In certain embodiments, the present invention relates to any one of the aforementioned polymers, wherein m is 8. In certain embodiments, the present invention relates to any one of the aforementioned polymers, wherein m is 9. In certain embodiments, the present invention relates to any one of the aforementioned polymers, wherein m is 10.

In certain embodiments, the present invention relates to any one of the aforementioned polymers, wherein p is 1. In certain embodiments, the present invention relates to any one of the aforementioned polymers, wherein p is 0.

In certain embodiments, the present invention relates to any one of the aforementioned polymers, wherein n is 1. In certain embodiments, the present invention relates to any one of the aforementioned polymers, wherein n is 2. In certain embodiments, the present invention relates to any one of the aforementioned polymers, wherein n is 3. In certain embodiments, the present invention relates to any one of the aforementioned polymers, wherein n is 4. In certain embodiments, the present invention relates to any one of the aforementioned polymers, wherein n is 5. In certain embodiments, the present invention relates to any one of the aforementioned polymers, wherein n is 6. In certain embodiments, the present invention relates to any one of the aforementioned polymers, wherein n is 7. In certain embodiments, the present invention relates to any one of the aforementioned polymers, wherein n is 8. In certain embodiments, the present invention relates to any one of the aforementioned polymers, wherein n is 9. In certain embodiments, the present invention relates to any one of the aforementioned polymers, wherein n is 10.

In certain embodiments, the present invention relates to any one of the aforementioned polymers, wherein Y is O. In certain embodiments, the present invention relates to any one of the aforementioned polymers, wherein Y is N(H). In certain embodiments, the present invention relates to any one of the aforementioned polymers, wherein Y is $C(H)_2$.

In certain embodiments, the present invention relates to any one of the aforementioned polymers, wherein the polymer further comprises one terminal subunit represented by formula V:

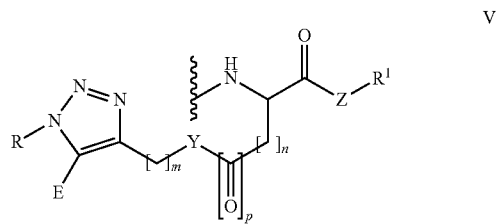

or a tautomer, enantiomer or stereoisomer thereof;

wherein, independently for each occurrence,

Z is N(H) or O;

$R^1$ is hydrogen, alkyl,

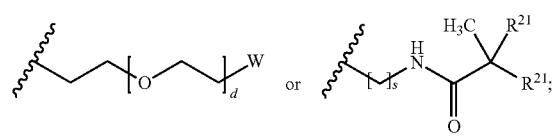

d is about 10 to about 300;

s is 1-5;

W is hydroxy, alkoxy, aryloxy, heteroaryloxy, aralkoxy or heteroaralkoxy;

$R^{21}$ is

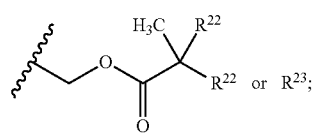

$R^{22}$ is

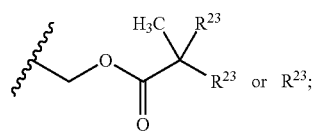

$R^{23}$ is

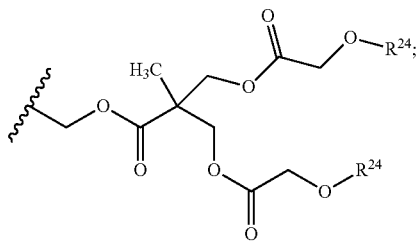

and
$R^{24}$ is

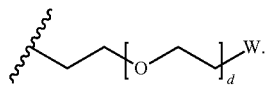

In certain embodiments, the present invention relates to any one of the aforementioned polymers, wherein Z is N(H). In certain embodiments, the present invention relates to any one of the aforementioned polymers, wherein $R^1$ is hydrogen. In certain embodiments, the present invention relates to any one of the aforementioned polymers, wherein $R^1$ is alkyl. In certain embodiments, the present invention relates to any one of the aforementioned polymers, wherein Z is N(H); and $R^1$ is heptyl.

In certain embodiments, the present invention relates to any one of the aforementioned polymers, wherein Z is O. In certain embodiments, the present invention relates to any one of the aforementioned polymers, wherein $R^1$ is hydrogen. In certain embodiments, the present invention relates to any one of the aforementioned polymers, wherein $R^1$ is alkyl. In certain embodiments, the present invention relates to any one of the aforementioned polymers, wherein Z is O; and $R^1$ is heptyl.

In certain embodiments, the present invention relates to any one of the aforementioned polymers, wherein $R^1$ is

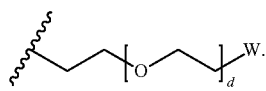

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150.

In certain embodiments, the present invention relates to any one of the aforementioned polymers, wherein W is hydroxy. In certain embodiments, the present invention relates to any one of the aforementioned polymers, wherein W is alkoxy. In certain embodiments, the present invention relates to any one of the aforementioned polymers, wherein W is methoxy.

In certain embodiments, the present invention relates to any one of the aforementioned polymers, wherein W is a protected hydroxy. In certain embodiments, the present invention relates to any one of the aforementioned polymers, wherein W is alkoxy. For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$). In certain embodiments, the present invention relates to any one of the aforementioned polymers, wherein W is methoxy. In certain embodiments, the present invention relates to any one of the aforementioned polymers, wherein W is acyloxy. In certain embodiments, the present invention relates to any one of the aforementioned polymers, wherein W is alkylcarbonyloxy.

In certain embodiments, the present invention relates to any one of the aforementioned polymers, wherein W is a protected amino, for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), or as a 2-(phenylsulfonyl)ethyloxy amide (—NHPsec).

In certain embodiments, the present invention relates to any one of the aforementioned polymers, wherein $R^1$ is

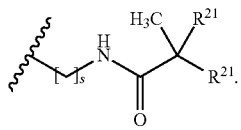

In certain embodiments, the present invention relates to any one of the aforementioned polymers, wherein Z is N(H); $R^1$ is

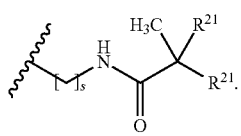

In certain embodiments, the present invention relates to any one of the aforementioned polymers, wherein s is 1. In certain embodiments, the present invention relates to any one of the aforementioned polymers, wherein s is 2. In certain embodiments, the present invention relates to any one of the aforementioned polymers, wherein s is 3. In certain embodiments, the present invention relates to any one of the aforementioned polymers, wherein s is 4. In certain embodiments, the present invention relates to any one of the aforementioned polymers, wherein s is 5.

In certain embodiments, the present invention relates to any one of the aforementioned polymers, wherein $R^{21}$ is

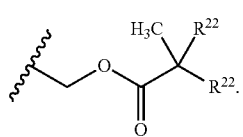

In certain embodiments, the present invention relates to any one of the aforementioned polymers, wherein $R^{22}$ is

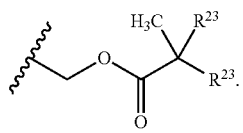

In certain embodiments, $R^1$ may be a dendrimer, such as those described in Tian L, Hammond P T, "Comb-dendritic block copolymers as tree-shaped macromolecule amphiphiles for nanoparticle self-assembly", *Chemistry of Materials* 2006, 18, 3976-3984; and Tian L, Nguyen P, Hammond P T, "Vesicular self-assembly of comb-dendritic block copolymers", *Chem. Commun.* 2006, 33, 3489-3491; both of which are hereby incorporated by reference.

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150.

In certain embodiments, the present invention relates to any one of the aforementioned polymers, wherein W is hydroxy. In certain embodiments, the present invention relates to any one of the aforementioned polymers, wherein W is alkoxy. In certain embodiments, the present invention relates to any one of the aforementioned polymers, wherein W is methoxy.

In certain embodiments, the present invention relates to any one of the aforementioned polymers, wherein W is a protected hydroxy. In certain embodiments, the present invention relates to any one of the aforementioned polymers, wherein W is alkoxy. For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$). In certain embodiments, the present invention relates to any one of the aforementioned polymers, wherein W is methoxy. In certain embodiments, the present invention relates to any one of the aforementioned polymers, wherein W is acyloxy. In certain embodiments, the present invention relates to any one of the aforementioned polymers, wherein W is alkylcarbonyloxy.

In certain embodiments, the present invention relates to any one of the aforementioned polymers, wherein W is a protected amino, for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), or as a 2-(phenylsulfonyl)ethyloxy amide (—NHPsec).

Certain aspects of the invention relates to co-polymers which comprise the subunits described above and additional subunits. For example, in certain embodiments, the present invention relates to any one of the aforementioned polymers, wherein the polymer further comprises a plurality of subunits represented by formula VI:

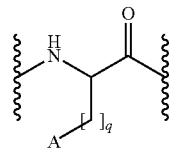

VI or a tautomer, enantiomer or stereoisomer thereof;
wherein, independently for each occurrence,
A is hydrogen, alkyl, alkoxy, carboxy, alkoxycarbonyl, amino, amido, thio, alkylthio, aryl, or heteroaryl; and
q is 0-10.

In certain embodiments, the present invention relates to any one of the aforementioned polymers, wherein the polymer comprises between about 5 and about 300 subunits of formula VI. In certain embodiments, the present invention relates to any one of the aforementioned polymers, wherein the polymer comprises between about 5 and about 50 subunits of formula VI. In certain embodiments, the present invention relates to any one of the aforementioned polymers, wherein the polymer comprises between about 50 and about 100 subunits of formula VI. In certain embodiments, the present invention relates to any one of the aforementioned polymers, wherein the polymer comprises between about 100 and about 150 subunits of formula VI. In certain embodiments, the present invention relates to any one of the aforementioned polymers, wherein the polymer comprises between about 150 and about 200 subunits of formula VI. In certain embodiments, the present invention relates to any one of the aforementioned polymers, wherein the plurality of subunits of formula II are connected to form a block and the plurality of subunits of formula VI are connected to form a block.

In certain embodiments, the present invention relates to any one of the aforementioned polymers, wherein q is 0. In certain embodiments, the present invention relates to any one of the aforementioned polymers, wherein q is 1. In certain embodiments, the present invention relates to any one of the aforementioned polymers, wherein q is 2. In certain embodiments, the present invention relates to any one of the aforementioned polymers, wherein q is 3. In certain embodiments, the present invention relates to any one of the aforementioned polymers, wherein q is 4. In certain embodiments, the present invention relates to any one of the aforementioned polymers, wherein q is 5. In certain embodiments, the present invention relates to any one of the aforementioned polymers, wherein q is 6. In certain embodiments, the present invention relates to any one of the aforementioned polymers, wherein q is 7. In certain embodiments, the present invention relates to any one of the aforementioned polymers, wherein q is 8. In certain embodiments, the present invention relates to any one of the aforementioned polymers, wherein q is 9. In certain embodiments, the present invention relates to any one of the aforementioned polymers, wherein q is 10.

In certain embodiments, the present invention relates to any one of the aforementioned polymers, wherein the polymer further comprises one terminal subunit represented by formula VII:

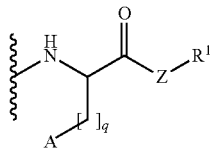

VII or a tautomer, enantiomer or stereoisomer thereof; wherein
Z is —N(H)— or —O—;
$R^1$ is hydrogen, alkyl,

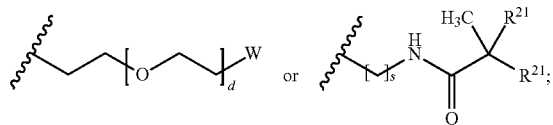

d is about 10 to about 300;
s is 1-5;
W is hydroxy, alkoxy, aryloxy, heteroaryloxy, aralkoxy or heteroaralkoxy;
$R^{21}$ is

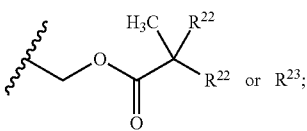

$R^{22}$ is

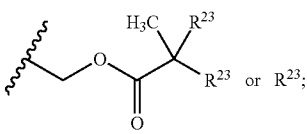

$R^{23}$ is

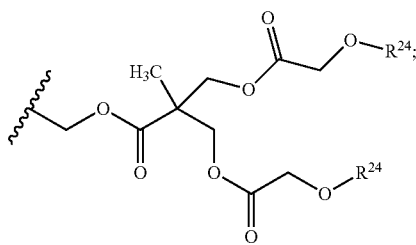

and
$R^{24}$ is

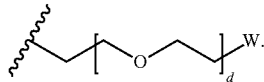

In certain embodiments, the present invention relates to any one of the aforementioned polymers, wherein Z is N(H). In certain embodiments, the present invention relates to any one of the aforementioned polymers, wherein $R^1$ is hydrogen. In certain embodiments, the present invention relates to any one of the aforementioned polymers, wherein $R^1$ is alkyl. In certain embodiments, the present invention relates to any one of the aforementioned polymers, wherein Z is N(H); and $R^1$ is heptyl.

In certain embodiments, the present invention relates to any one of the aforementioned polymers, wherein Z is O. In certain embodiments, the present invention relates to any one of the aforementioned polymers, wherein $R^1$ is hydrogen. In certain embodiments, the present invention relates to any one of the aforementioned polymers, wherein $R^1$ is alkyl. In certain embodiments, the present invention relates to any one of the aforementioned polymers, wherein Z is O; and $R^1$ is heptyl.

In certain embodiments, the present invention relates to any one of the aforementioned polymers, wherein $R^1$ is

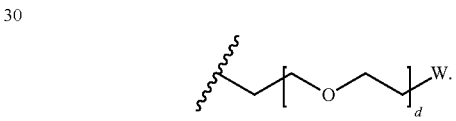

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150.

In certain embodiments, the present invention relates to any one of the aforementioned polymers, wherein W is hydroxy. In certain embodiments, the present invention relates to any one of the aforementioned polymers, wherein W is alkoxy. In certain embodiments, the present invention relates to any one of the aforementioned polymers, wherein W is methoxy.

In certain embodiments, the present invention relates to any one of the aforementioned polymers, wherein W is a protected hydroxy. In certain embodiments, the present invention relates to any one of the aforementioned polymers, wherein W is alkoxy. For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)

CH$_3$). In certain embodiments, the present invention relates to any one of the aforementioned polymers, wherein W is methoxy. In certain embodiments, the present invention relates to any one of the aforementioned polymers, wherein W is acyloxy. In certain embodiments, the present invention relates to any one of the aforementioned polymers, wherein W is alkylcarbonyloxy.

In certain embodiments, the present invention relates to any one of the aforementioned polymers, wherein W is a protected amino, for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), or as a 2-(phenylsulfonyl)ethyloxy amide (—NHPsec).

In certain embodiments, the present invention relates to any one of the aforementioned polymers, wherein R$^1$ is

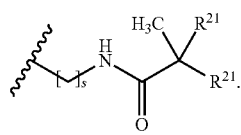

In certain embodiments, the present invention relates to any one of the aforementioned polymers, wherein Z is N(H); R$^1$ is

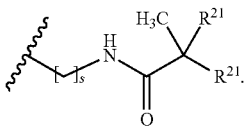

In certain embodiments, the present invention relates to any one of the aforementioned polymers, wherein s is 1. In certain embodiments, the present invention relates to any one of the aforementioned polymers, wherein s is 2. In certain embodiments, the present invention relates to any one of the aforementioned polymers, wherein s is 3. In certain embodiments, the present invention relates to any one of the aforementioned polymers, wherein s is 4. In certain embodiments, the present invention relates to any one of the aforementioned polymers, wherein s is 5.

In certain embodiments, the present invention relates to any one of the aforementioned polymers, wherein R$^{21}$ is

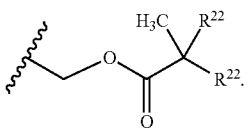

In certain embodiments, the present invention relates to any one of the aforementioned polymers, wherein R$^{22}$ is

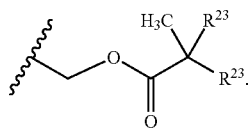

In certain embodiments, the present invention relates to any one of the aforementioned polymers, wherein d is about 10 to about 150. In certain embodiments, the present invention relates to any one of the aforementioned polymers, wherein d is about 10 to about 25. In certain embodiments, the present invention relates to any one of the aforementioned polymers, wherein d is about 25 to about 50. In certain embodiments, the present invention relates to any one of the aforementioned polymers, wherein d is about 50 to about 75. In certain embodiments, the present invention relates to any one of the aforementioned polymers, wherein d is about 75 to about 100. In certain embodiments, the present invention relates to any one of the aforementioned polymers, wherein d is about 100 to about 125. In certain embodiments, the present invention relates to any one of the aforementioned polymers, wherein d is about 125 to about 150. In certain embodiments, the present invention relates to any one of the aforementioned polymers, wherein W is hydroxy. In certain embodiments, the present invention relates to any one of the aforementioned polymers, wherein W is alkoxy. In certain embodiments, the present invention relates to any one of the aforementioned polymers, wherein W is methoxy.

In certain embodiments, the present invention relates to any one of the aforementioned polymers, including copolymers, wherein the polypeptide backbone has a substantial α-helical conformation.

In certain embodiments, the present invention relates to any one of the aforementioned polymers, including copolymers, wherein the number average molecular weight is between about 100 Daltons and about 2,000,000 Daltons. In certain embodiments, the present invention relates to any one of the aforementioned polymers, including copolymers, wherein the number average molecular weight is between about 100 Daltons and about 1,000,000 Daltons. In certain embodiments, the present invention relates to any one of the aforementioned polymers, including copolymers, wherein the number average molecular weight is between about 1,000,000 Daltons and about 2,000,000 Daltons. In certain embodiments, the present invention relates to any one of the aforementioned polymers, including copolymers, wherein the number average molecular weight is between about 1,400,000 Daltons and about 1,600,000 Daltons.

Preparation of Monomers and Polymers

Figure 10:
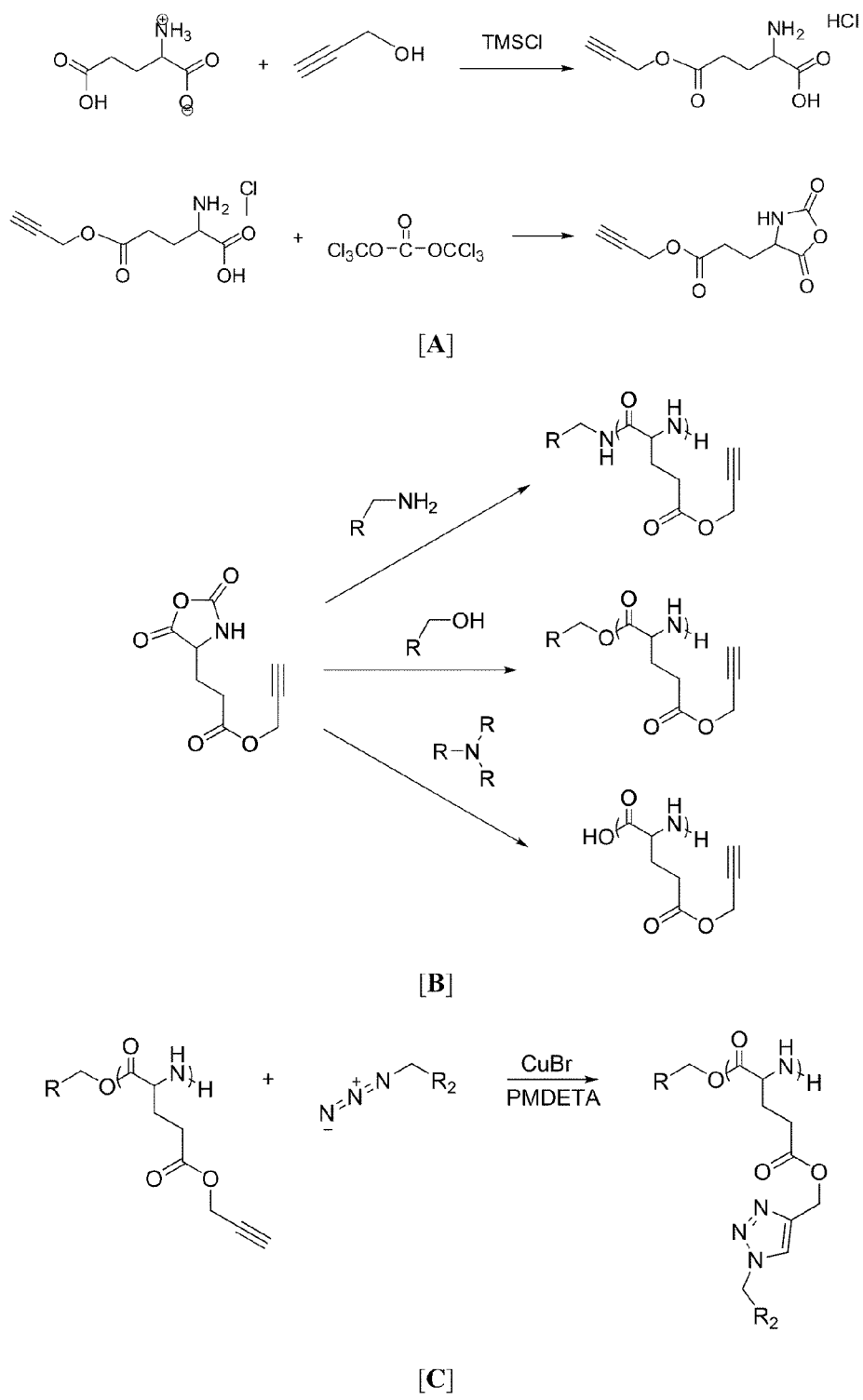
FIG. 10 depicts an exemplary route to the various monomers and polymers of the invention.

Polypeptides, such as poly(propargyl-L-glutamate) (PPLG), may be synthesized by a quasi living ring-opening polymerization (ROP) of N-carboxyanhydride (NCA) monomers. In certain embodiments, the polymer may contain an acetylene side group that is available for click chemistry. NCA monomers may be synthesized by a two-step process as shown in FIG. 10A. The first step involves the reaction of a propargyl alcohol (or other click chemistry containing nucleophile) with, for example, glutamic acid to form an ω-propargyl ester of L-glutamic acid. The reaction can be mediated by chlorotrimethylsilane. The second step is the formation of the N-carboxy anhydride which is formed by reacting, in the case of the example shown, propargyl L-glutamic acid with triphosegene.

The ring opening polymerization of NCAs may be initiated by a couple of different methods, as shown in FIG. 10B. Any initiator containing a primary amine or an alcohol can be used. In addition, the initiator can be a macroinitiator, such as an amine-terminated polyethylene glycol or a small molecule initiator. The polymerization may also be initiated by a tertiary amine to create a homopolymer without the initiator being incorporated into the polymer backbone. Mono and bis(silyl) amides, as well as transition metal complexes, such as nickel-containing complexes, may also be used as initiators.

Selected Applications of Polymers

A wide variety of molecules can be "clicked" onto the polymers of the invention to create unique polypeptides, as shown in FIG. 10C for PPLG. Several examples of "clickable" molecules include but are not limited to terminated polymers which can be grafted onto the polymer at a high grafting efficiency, small molecules which can be used to introduce pH responsiveness, small molecule drugs, fluorescent dyes and/or radiolabels. As with polypeptides in general, the polymers of the invention may be used for, for example, drug delivery, tissue engineering, sensing and/or catalysis. Deming, T. J. *Adv. Drug Delivery Rev.* 2002, 54, 1145-1155; Wang, X. Y.; Kim, H. J.; Wong, C.; Vepari, C.; Matsumoto, A.; Kaplan, D. L. *Mater. Today* 2006, 9, 44-53; Dos Santos, S.; Chandravarkar, A.; Mandal, B.; Mimna, R.; Murat, K.; Saucede, L.; Tella, P.; Tuchscherer, G.; Mutter, M. *J. Am. Chem. Soc.* 2005, 127, 11888-11889; and Mart, R. J.; Osborne, R. D.; Stevens, M. M.; Ulijn, R. V. *Soft Matter* 2006, 2, 822-835. The polymers of the invention may also be used for, for example, nucleic acid (e.g., gene, siRNA) delivery, in responsive membranes (e.g., light responsive, pH responsive and temperature responsive), in display devices, in optical storage, and as adhesives.

Another aspect of the invention relates to a nanoparticle comprising a plurality of any one or more of the aforementioned polymers. Specifically, certain polymers of the invention by nature of their overall cationic charge can be used to transport polyanions, such a DNA and RNA. In certain embodiments, the present invention relates to any one of the aforementioned nanoparticles, further comprising a nucleic acid. In certain embodiments, the present invention relates to any one of the aforementioned nanoparticles, further comprising an siRNA. In certain embodiments, the present invention relates to any one of the aforementioned nanoparticles, wherein said polymers comprise pendant amines.

Exemplification

The invention, now being generally described, will be more readily understood by reference to the preparation and evaluation of poly(propargyl-L-glutamate) (PPLG), and the attachment of different lengths of azide-terminated polyethylene glycol (PEG) to the PPLG, which is provided below. This model system demonstrates the high efficiency of "grafting onto" polymer side chains, while maintaining the α-helical conformation of the polypeptide backbone. The discussion of this model system is included for purposes of illustration and is not intended to limit the invention.

Materials and Methods

All chemicals were used as received. Anhydrous 99.8% DMF, purchased from Sigma Aldrich was used for polymerization and click reactions. PEG-NH$_2$ was purchase from NOF Corporation. The azide terminated poly(ethylene glycol) was synthesized according to the literature procedure (H. F. Gao, K. Matyjaszewski, *J. Am. Chem. Soc.* 2007, 129, 6633).

$^1$H NMR and $^{13}$C NMR were recorded on Bruker 400 MHz spectrometers. Fourier transform infrared (FTIR) spectra were recorded on a Thermo Nicolet NEXUS 870 series spectrophotometer.

Gel permeation chromatography (GPC) measurements were carried out using a Water Breeze 1525 HPLC system equipped with two Polypore HT columns operated at 75° C., series 2414 refractive index detector, series 1525 binary HPLC pump, and 717 plus autosampler. Waters' Breeze Chromatography Software Version 3.30 was used for data collection as well as data processing. DMF was used all the time as eluent for analysis and as solvent for sample preparation. The average molecular weight of the sample was calibrated against narrow molecular weight poly(methyl methacrylate) standards.

Circular dichroism (CD) spectroscopy of polymer solution was carried out by using an Aviv model 202 CD spectrometer. Measurements were performed at 25±0.1° C., sampling every 1 nm with a 3 s averaging time over the range of 190-260 nm (bandwidth=1.0 nm).

Preparation and Characterization of Poly(γ-propargyl L-Glutamate) (PPLG)

As shown in FIG. 1A, the alkyne containing monomer, γ-propargyl L-glutamate N-carboxyanhydride (2), was synthesized by a two-step process. γ-Propargyl L-glutamate hydrochloride (1) was prepared by the reaction a propargyl alcohol with glutamic acid mediated by chlorotrimethylsilane; and (1) was then reacted with triphosgene in ethyl acetate to form the NCA monomer (2). The NCA monomer (2) was characterized by $^1$H NMR and FTIR.

As described below, PPLG (3) was prepared by ROP of (2), initiated with heptylamine initiator in dimethylformamide (DMF). The polymerization was monitored by observing the disappearance of the NCA characteristic peaks (1790 and 1850 cm$^{-1}$) on an FTIR spectrum. The peaks disappeared after 2-3 days and the polymer was purified by precipitation into diethyl ether. The resulting PPLG had a degree of polymerization of n=40 (by DMF GPC, Mn=8513, PDI=1.449). The relatively broad molecular weight distribution is typical of a primary amine initiated NCA ROP.

Synthesis of γ-propargyl L-glutamate hydrochloride (1). (1) was synthesized following the procedure presented by Belshaw et al. (P. J. Belshaw, S. Mzengeza, G. A. Lajoie, *Synth. Commun.* 1990, 20, 3157). L-glutamic acid (10 g, 68 mmol) was suspended in propargyl alcohol (330 mL) under argon. Chlorotrimethylsilane (17.27 mL, 136 mmol) was added dropwise to the suspension. The resulting solution was stirred at room temperature for two days until there was no undissolved L-glutamic acid. The reaction solution was precipitated into diethyl ether giving a white solid. The product was filtered, washed with diethyl ether, and dried under vacuum to yield 12.37 g (82%). $^1$H NMR (400 MHz, D$_2$O) δ=2.20 (m, 2H, CH$_2$), 2.63 (dt, 2H, CH—CO), 2.86 (t, 1H, C≡CH), 4.05 (t, 1H, CH), 4.69 (d, 2H, CH$_2$CO).

Synthesis of N-carboxyanhydride of γ-propargyl L-glutamate (2). (2) was synthesized following a the procedure presented by Poche et al. (D. S. Poche, M. J. Moore, J. L. Bowles, *Synth. Commun.* 1999, 29, 843). (1) (1.35 g, 6.13 mmol) was suspended in dry ethyl acetate (50 mL) and the solution was heated to reflux. Triphosegene (0.61 g, 2.04 mmol) was added and the reaction was refluxed for 4-5 hours under N$_2$. The reaction solution was cooled to room temperature and any unreacted (1) was removed by filtration. The reaction solution was then cooled to 5° C. and washed with 50 mL of water, 50 mL of saturated sodium bicarbonate, and 50 mL of brine all at 5° C. The solution was then dried with magnesium sulfate, filtered, and concentrated down to viscous oil (0.66 g, 43% yield). $^1$H NMR (400 MHz, CDCl$_3$) δ=2.20 (dm, 2H, CH$_2$), 2.49 (t, 1H, C≡CH), 2.58 (t, 2H, CH—CO), 4.39 (t, 1H, CH), 4.68 (d, 2H, CH$_2$CO), 6.5 (s, 1H, NH).

Synthesis of Poly(γ-propargyl L-glutamate) (PPLG) initiated by heptylamine (3). A typical procedure for the polymerization is as follows. A round bottom flask was rinsed with acetone and oven dried. Under argon, (2) (1.72 g, 8.15 mmol) was dissolved in dry DMF (17 mL) and heptylamine (0.015 g, 0.13 mmol) was added. The reaction mixture was stirred for three days at room temperature. The polymer was precipitated into diethylether and removed by centrifugation (0.8646 g, 54% yield). $^1$H NMR (400 MHz, [D$_6$] DMF) δ=2.28 (dm, 2H, CH$_2$), 2.55 (dm, 2H, CH—CO), 3.38 (m, 1H, C≡CH), 4.09 (m, 1H, CH), 4.76 (m, 2H, CH$_2$CO), 8.5 (m, 1H, NH). HRMS m/z (ESI, M+NA$^+$) calculated 212.0553, found 212.0563.

Preparation and Characterization of Poly(Ethylene Glycol)-G-Poly(γ-Propargyl L-Glutamate) (PEG-g-PPLG)

A wide variety of molecules can be "clicked" onto the PPLG to create unique polypeptides. In order to react with the alkynes of the PPLG, "clickable" molecules may contain an azide linkage.

For example, to synthesize PPLG-g-PEG, the PPLG was coupled with PEG-N$_3$ using CuBr/PMDETA as catalyst in DMF with a molar ratio of alkyne/azide/CuBr/PMDETA equal to 1/2/0.33/0.33 for all molecular weight PEG-N$_3$ and at various ratios for PEG1000-N$_3$ to further characterize the side chain grafting. After 35 minutes, the reaction was complete and the reaction solution was passed through a short alumina oxide column to remove the catalyst. The functionalized polymers were purified by dialysis and characterized by $^1$H NMR, FTIR, GPC, and circular dichroism.

Figure 6:
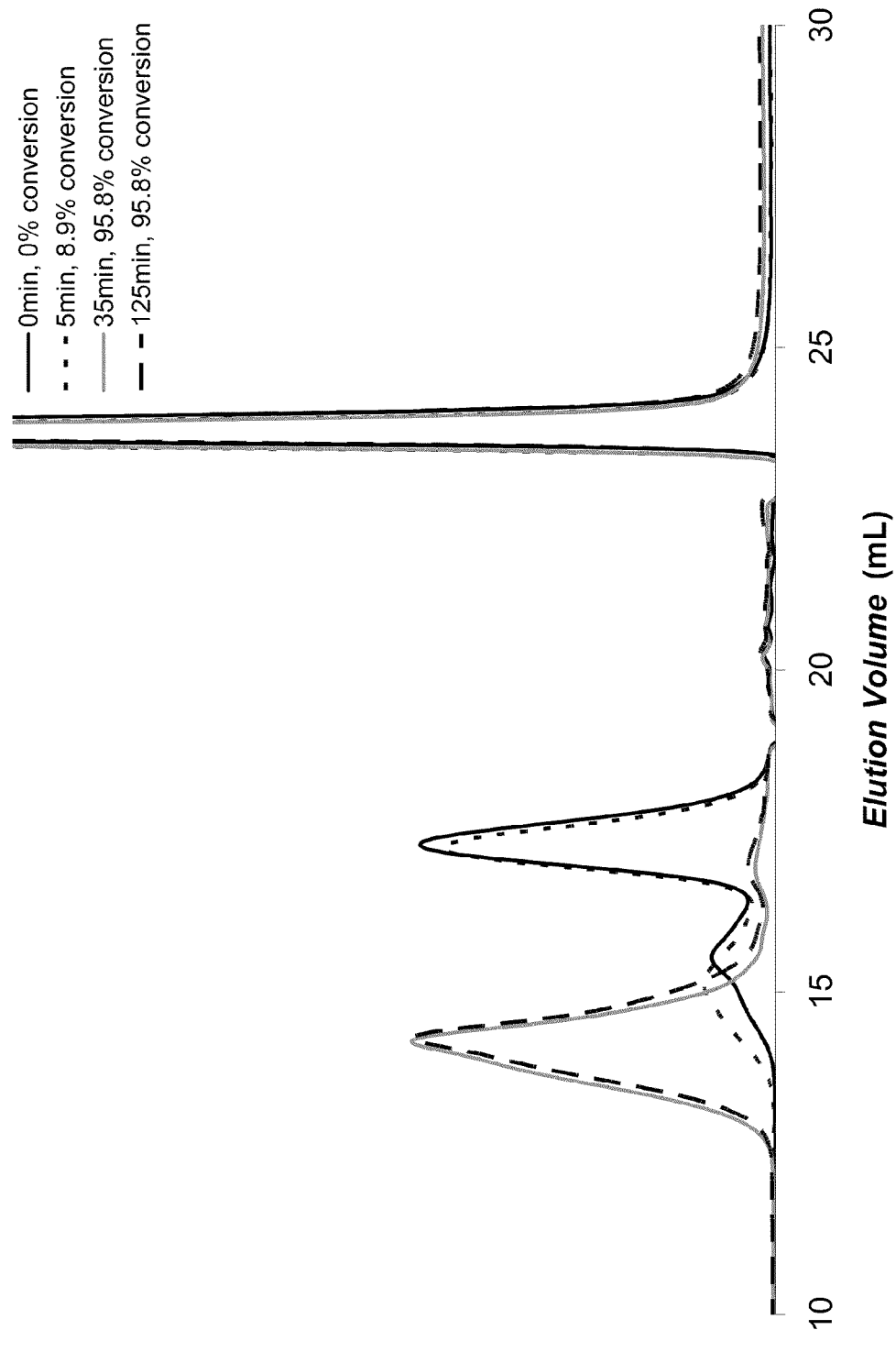
FIG. 6 depicts DMF GPC traces as a function of reaction time.

The kinetics of the PEG-N$_3$ coupling reaction was determined using a PEG1000-N$_3$ side chain and a reaction molar ratio of alkyne/azide/CuBr/PMDETA equal to 1/1/0.1/0.1 using GPC. The molar ratios were lowered to slow down the kinetics such that they could be observed by GPC. Samples were taken from the reaction mixture (40 μL) at various time points and GPC samples were prepared by dilution with 750 μL DMF and addition of 5 μL of toluene as an internal standard. Conversion of the PEG-N$_3$ was determined by comparing the peak area of the PEG-N$_3$ curve to the toluene standard. FIG. 6 shows the DMF GPC traces and the conversion as a function of reaction time. As indicated by the overlap of the 125 min trace and the 35 minute trace, the reaction was complete after 35 minutes. The conversion of PEG-N$_3$ by GPC at 35 minutes was 95.8%.

Figure 7:
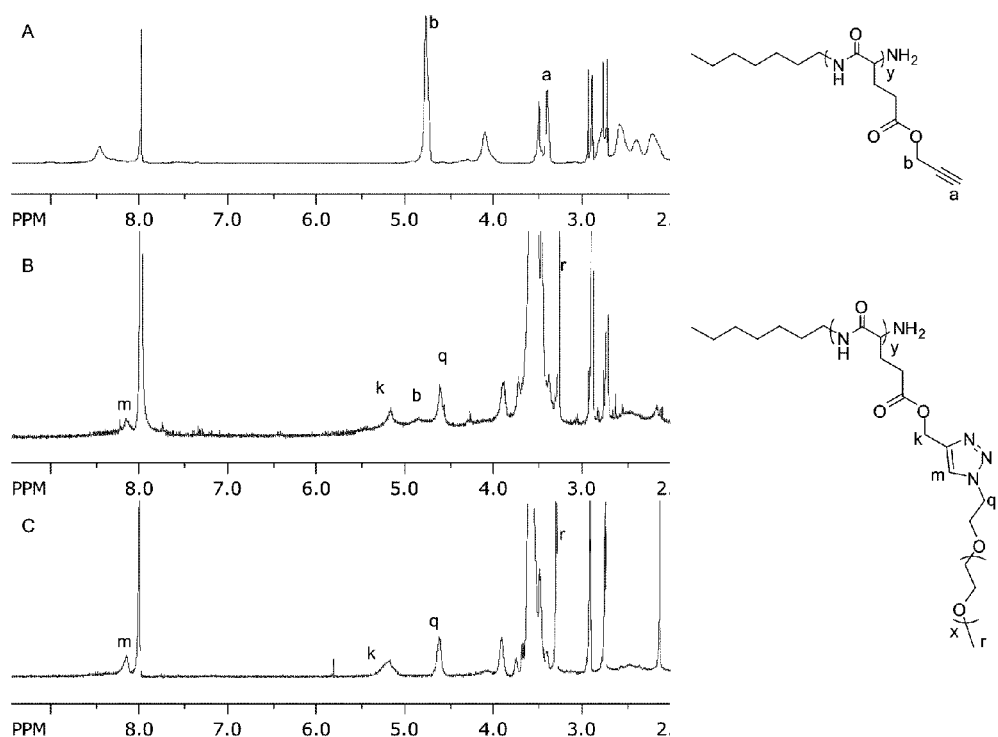
FIG. 7 depicts a $^1$H NMR spectrum of [A] PPLG in DMF-$d_7$; [B] PPLG-g-PEG 1000 with a feed ratio PPLG/PEG-$N_3$ of 1/0.5 in DMF-$d_7$; and [C] PPLG-g-PEG 1000 with a feed ratio PPLG/PEG-$N_3$ of 1/2 in DMF-$d_7$.

$^1$H NMR was also used to monitor side chain grafting. FIG. 7 shows the $^1$H NMR spectrum of PPLG, PPLG-g-PEG1000 at 50% functionalization, and PPLG-g-PEG at nearly complete functionalization. When comparing FIG. 7A to FIG. 7B, the ester peak, b, has decreased and a new ester peak, k, has appeared; furthermore, the m peak, representing the methyl group next to the nitrogen of the triazole group appears. The alkyne peak, a, appears to also decrease but is not observed because it overlaps with the PEG-N$_3$ peaks. When comparing FIG. 7B to FIG. 7C, the ester peak, b, completely disappears and the appearance new ester peak, k, has further increased. In FIG. 7B and FIG. 7C, there are no peaks from the original backbone present that can be used to determine a grafting efficiency. To determine the grafting efficiency, a small sample of the crude reaction solution was concentrated down to a solid, dissolved in DMF-d$^7$, and an $^1$H NMR was taken. From this sample, the conversion of the PEG-N$_3$ was determined by comparing the area under peaks m and f. Based on the conversion of the azide to triazole (for PPLG-g-PEG1000, y$_{conversion}$=49.6%) and the initial feed ratio of PEG-N$_3$ to PPLG (1/2.01), the grafting efficiency was determined (y$_{graft}$=99.6%). These results are consistent with those observed by DMF GPC for the PPLG-g-PEG1000 system. Similar NMR spectrum were observed for PPLG-g-PEG with PEG MW 1000, 2000, and 5000 g/mol. As shown in Table 1, the grafting efficiency of each molecular weight sample reacted with a feed ratio of PPLG/PEG-N$_3$ of 1/2 is close to 100%.

TABLE 1

| | Mn (g/mol) | Mp (g/mol) | PDI | y$_{graft}$ |
|---|---|---|---|---|
| PPLG | 7043 | 6870 | 1.38 | — |
| PPLG-g-PEG 750 | 14134 | 18080 | 1.42 | 98.9 ± 1.3% |
| PPLG-g-PEG 1000 | 14999 | 22223 | 1.40 | 96.3 ± 2.2% |
| PPLG-g-PEG 2000 | 34443 | 41884 | 1.22 | Not Tested |
| PPLG-g-PEG 5000 | 97082 | 99058 | 1.19 | 97.4 ± 2.8% |

Figure 8:
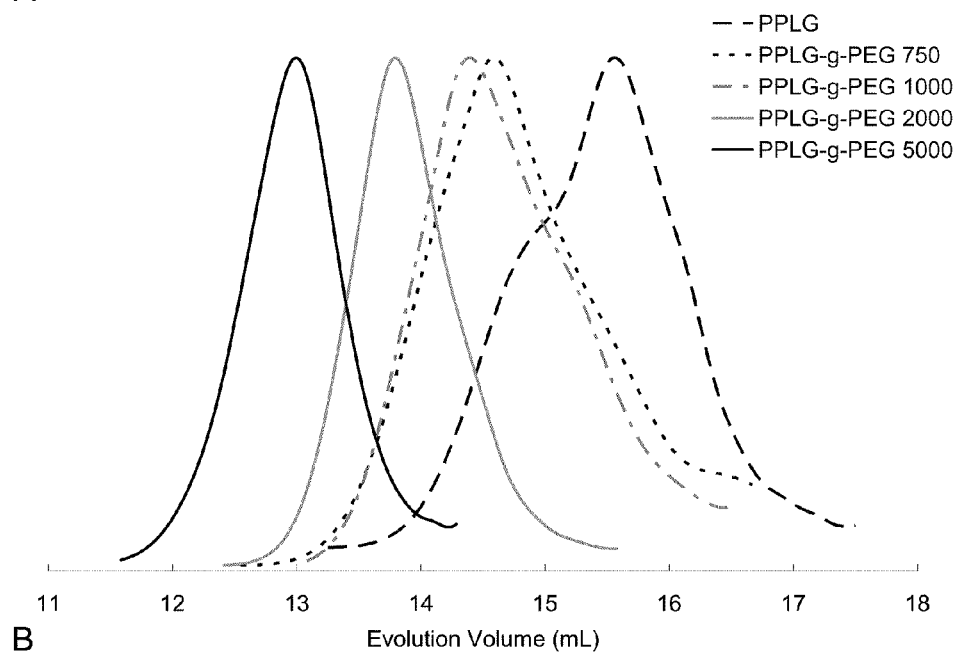
FIG. 8 depicts [A] DMF GPC traces for PPLG-g-PEG; and [B] PPLG-g-PEG molecular weight as a function of grafted PEG-$N_3$ molecular weight
Figure 8:
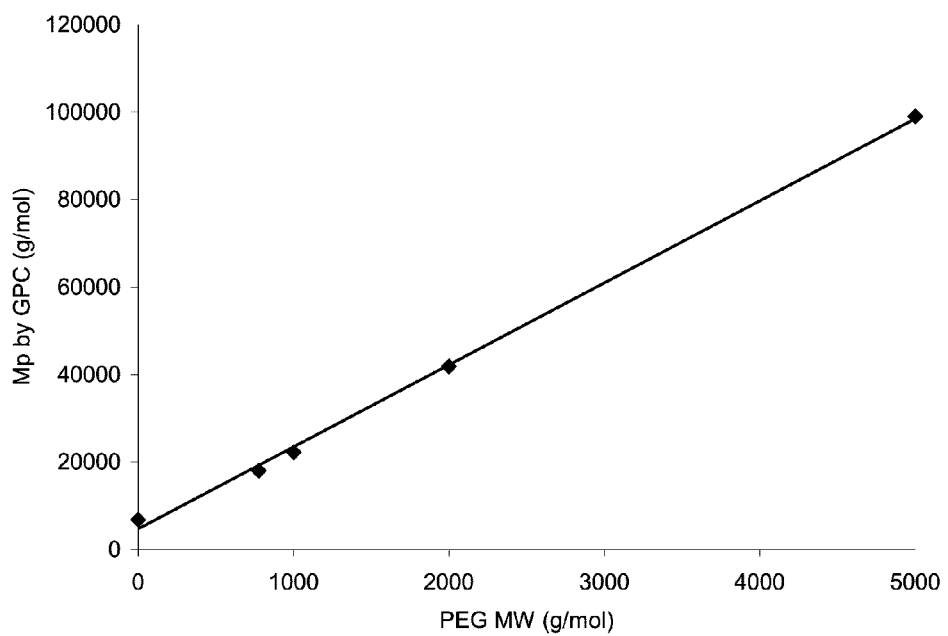

FIG. 8A shows the DMF GPC traces of different molecular weight PPLG-g-PEG polymers prepared with a PPLG/PEG ratio of 1/2. All of the grafted copolymers show an increase in molecular weight while maintaining a narrow molecular weight distribution. This molecular weight increase also indicates that the grafting method does not degrade the peptide backbone. In FIG. 8B, the PPLG-g-PEG molecular weight scales linearly with increasing side chain length indicating that the grafting efficiency is consistent for each side chain molecular weight.

The grafting efficiencies that were observed are higher than those of similar systems utilizing graft-onto approaches found in the literature, including those involving click chemistry. Gao and Matyjaszewski synthesized a similar system of PHEMA-g-PEG and the highest PEG-N$_3$ (MW=750) grafting efficiency obtained was 88.4% at an alkyne/azide ratio of 1/8.5 (H. F. Gao, K. Matyjaszewski, *J. Am. Chem. Soc.* 2007, 129, 6633). They suggest that the grafting efficiency is lower than 100% as a result of steric congestion. Parrish and Emrick reported PEG-grafted aliphatic polyester systems with PEG-N$_3$ up to 1100 molecular weight and grafting efficiencies between 70-80% (B. Parrish, T. Emrick, *Macromolecules* 2004, 37, 5863). Parrish, Breitenkamp, and Emrick reported a Poly(α-Propargyl-δ-valerolactone)-g-PEG system where the PEG-N$_3$ 1100 grafting efficiency obtained was 43% (B. Parrish, R. B. Breitenkamp, T. Emrick, *J. Am. Chem. Soc.* 2005, 127, 7404). While not intending to be bound by any theory, it is hypothesized that the high grafting efficiency of nearly 100%, achieved with PPLG is at least a part a result of the rigid α-helical structure of the polymer backbone. Synthetic peptides, in particular substituted poly(L-glutamates) form stable α-helix. Watanabe et al. reported a series of poly(γ-n-alkyl) L-glutamates) with alkyl chains ranging from 5-18 alkyl carbons, all assumed a right handed α-helical structure when solvent cast from dichloromethane (J. Watanabe, H. Ono, I. Uematsu, A. Abe, Macromolecules 2002, 18, 2141). Smith and Woody reported that poly(γ-n-dodecyl L-glutamate) adapted an α-helical conformation in various hydrocarbon solvents (J. C. Smith, R. W. Woody, *Biopolymers* 1973, 12, 2657). This stable α-helical structure causes the alkyne terminated side chains to protrude outward from each repeat unit increasing their availability for coupling. The α-helical structure is present throughout the reaction. Initially, the a-helical structure is from the PPLG backbone. Once the reaction reaches a high grafting density, the steric repulsion between the grafted PEG chains causes the graft polymer to develop the shape of a symmetrical brush polymer with the most favorable backbone conformation of an α-helix (L. Feuz, P. Strunz, T. Geue, M. Textor, O. Borisov, *Eur. Phys. J. E* 2007, 23, 237).

Figure 3:
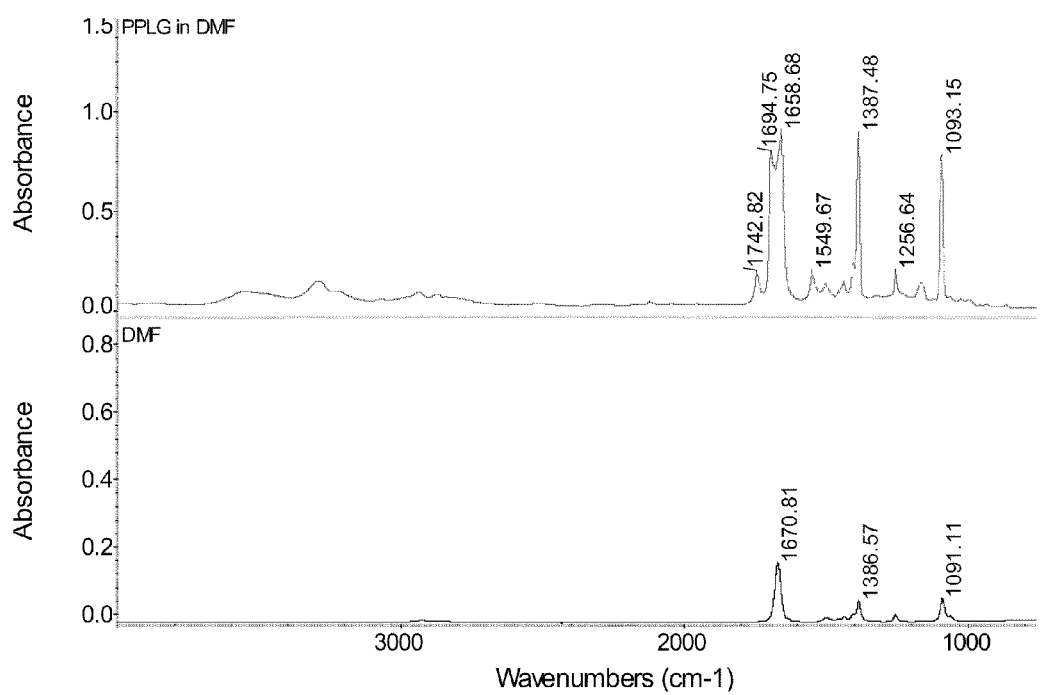
FIG. 3 depicts FTIR of PPLG in DMF; and FTIR of DMF.

To confirm the hypothesis that PPLG has an α-helical structure, liquid phase FTIR was performed on PPLG in DMF (52 mg/mL) using a zinc selenide cell with a path length of 0.015 mm. The α-helical conformation was identified by the strong C=O amide I absorption at 1658 cm$^{-1}$ and the N—H amide II absorption at 1549 cm$^{-1}$ (FIG. 3). In addition, circular dichroism (CD) was performed in water (DMF is not a suitable solvent for CD) to confirm the presences of an alpha helical structure in PPLG and PPLG-g-PEG at different grafting densities and with different molecular weight side chains. To obtain a CD spectra of PPLG, a block copolymer, PEG$_{114}$-b-PPLG$_{26.6}$ was synthesized (synthesis, characterization, and CD spectra are discussed in more detail below). Samples were prepared using a 1 mg/mL concentration for PEG-b-PPLG and 2.5 mg/mL polymer solution for all PPLG-g-PEG samples. CD measurements were taken using a cell with a 1 mm path length.

Figure 9:
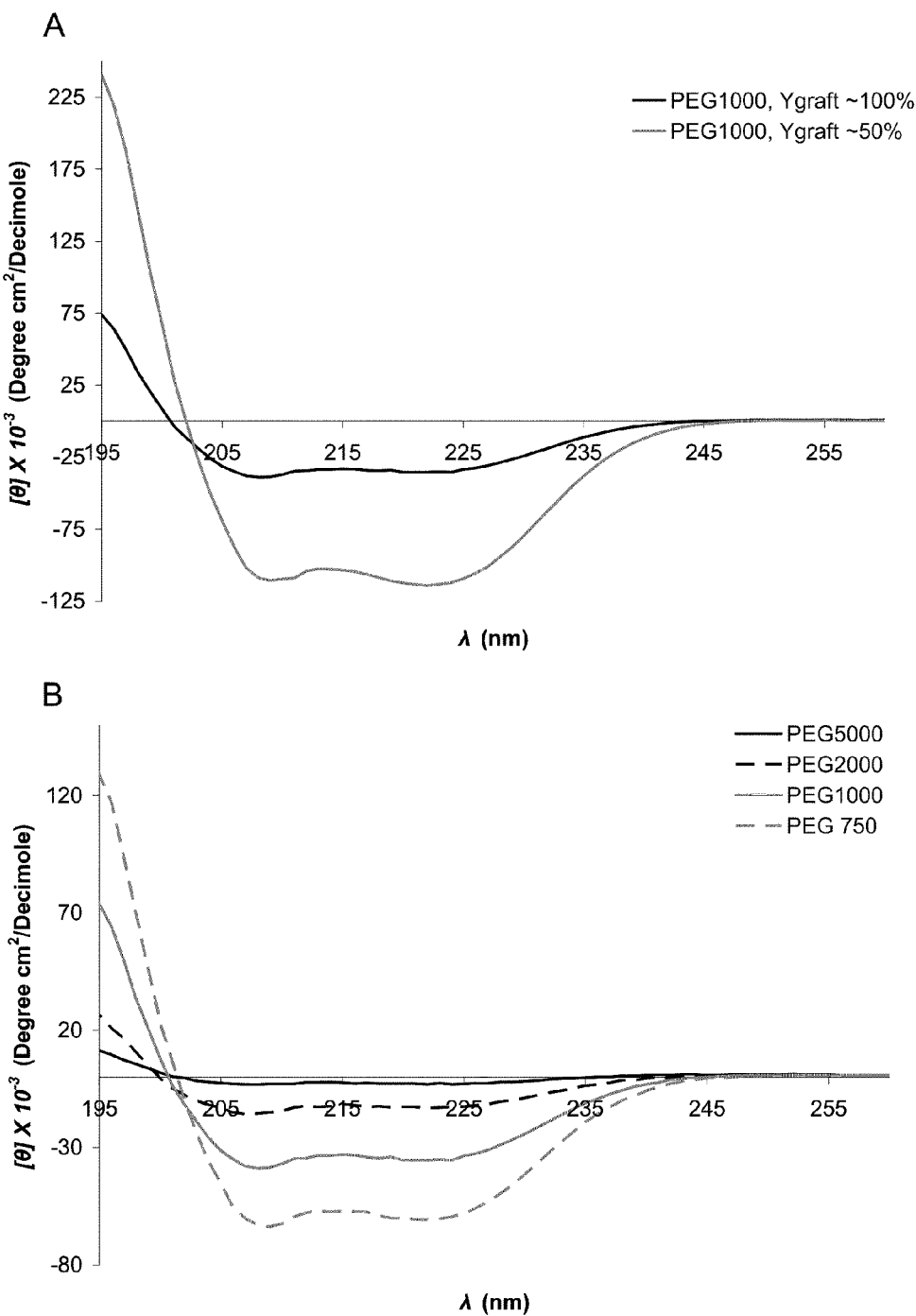
FIG. 9 depicts [A] CD of PPLG-g-PEG 1000 at about 50% and at about 100% grafting in water; and [B] CD of PPLG-g-PEG at different molecular weights all with close to 100% grafting.

For all samples, the characteristic negative ellipticity of an α-helix was observed at 208 nm and 222 nm. As shown in FIG. 9A, at 50% substitution and near 100% substitution, the backbone has an α-helical conformation. The increased minimums at 209 nm and 222 nm are a result of an increased presence of PEG side chains decreasing the concentration of α-helix backbone. In FIG. 9B, the characteristic α-helix minimum were observed for all molecular weight of the PEG side chains. The characteristic α-helix peaks observed in FTIR and CD indicate that the polymer backbone does have an alpha helix structure; the rotating helical arrangement of these groups may increase their availability along the backbone for coupling with the PEG-N$_3$ side chains.

Figure 5:
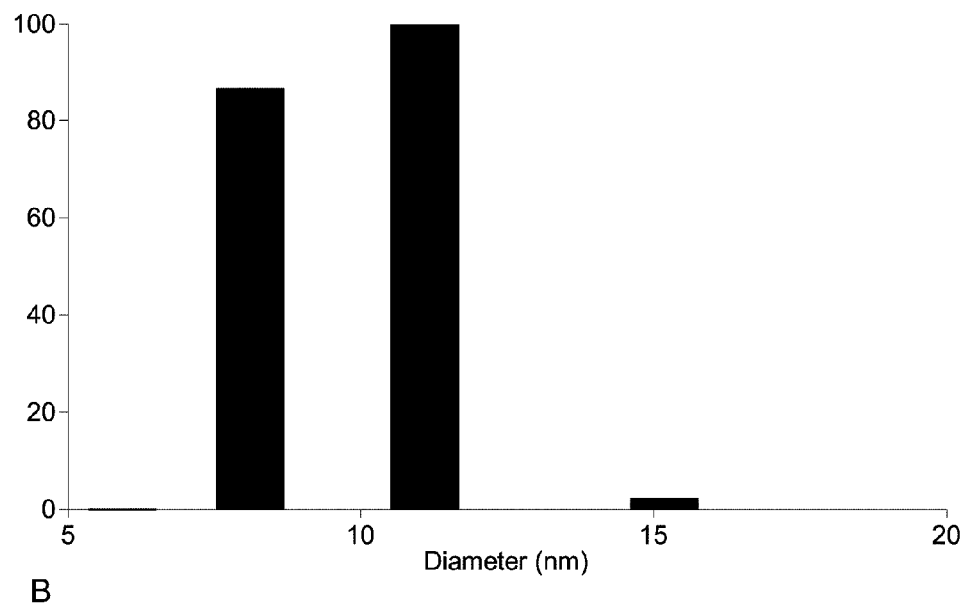
FIG. 5 depicts [A] particle size distribution for PPLG-g-PEG (MW 2000) recorded at 90°; and [B] particle size as a function of PEG side chain molecular weight.
Figure 5:
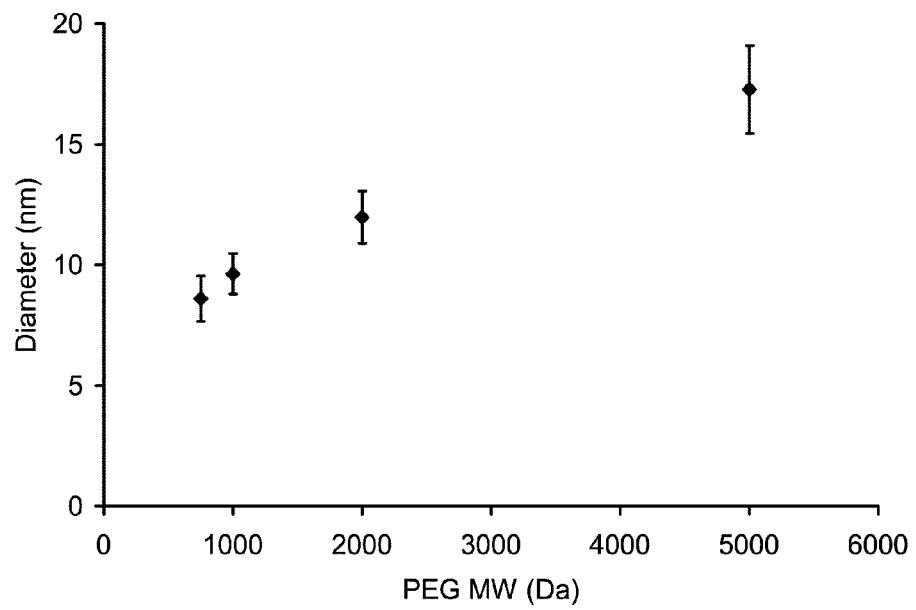

Dynamic light scattering was also used to observe the size of the molecular brushes obtained when different molecular weight side chains were grafted onto the PPLG. Measurements were taken at a 15° and 90° and similar distributions were observed for both angles. A representative size distribution for PPLG-g-PEG (MW1000) is shown in FIG. 5A. Narrow size distributions were obtained for all graft systems and particle size increases as a function of molecular weight, as shown in FIG. 5B.

Preparation and Characterization of Poly(Ethylene Glycol)-b-Poly(γ-Propargyl L-Glutamate) (PEG-b-PPLG).

Figure 2:
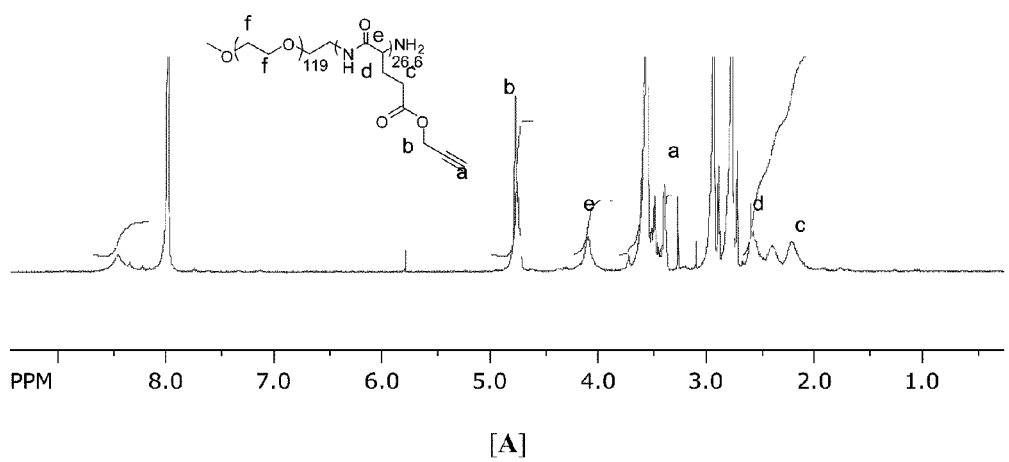
FIG. 2 depicts [A] $^1$H NMR of PEG-b-PPLG in DMF-$d_7$; and [B] GPC traces for $PEG_{114}$-b-$PPLG_{26.6}$.
Figure 2:
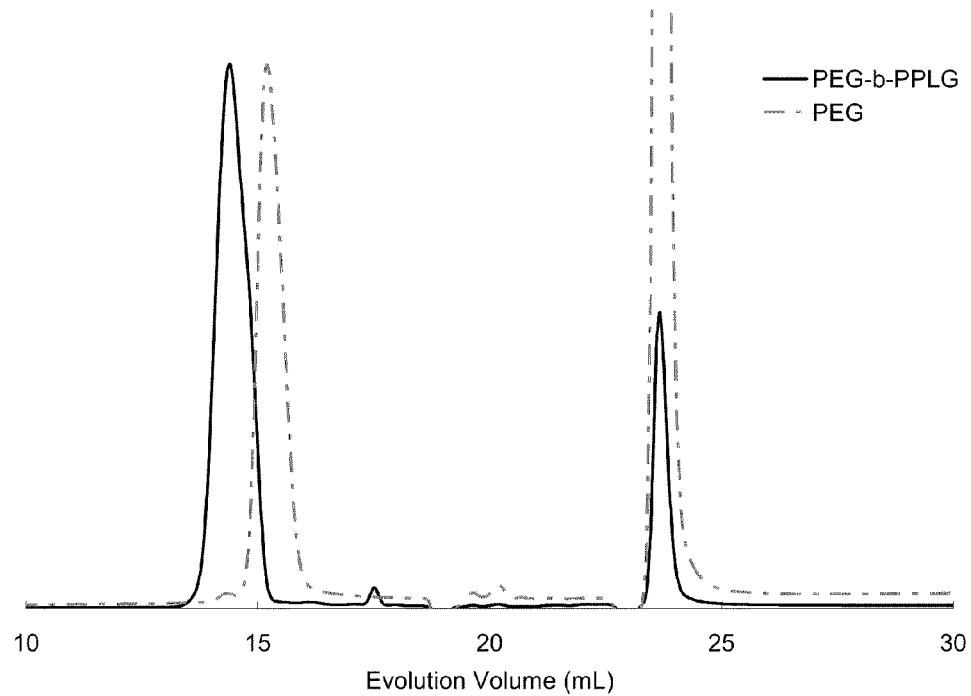

To verify by CD that PPLG has an α-helical structure, a PEG-b-PPLG diblock polymer was made. A typical procedure for the polymerization is as follows. A round bottom flask was rinsed with acetone and oven dried. In a glove box, (2) (0.327 g, 1.55 mmol) was dissolved in dry DMF (2.5 mL) in a round bottom flask. PEG-NH$_2$ (0.25 g, 0.05 mmol) was dissolved in DMF (2.5 mL) added to (2). The reaction mixture was stirred for three days at room temperature. The reaction solution was rotovaped and dried under vacuum to remove the DMF. The polymer was dissolved in dichloromethane precipitated into diethylether and removed by centrifugation. The NMR and GPC traces are shown in FIG. 2; and Table 2 summarizes the molecular weights obtained from NMR and GPC.

TABLE 2

| | From Vendor | From NMR | From GPC | | | |
|---|---|---|---|---|---|---|
| | Mp | Mn | Mn | Mw | Mp | PDI |
| PEG (MW 5000) | 5229 | | 8627 | 9297 | 9759 | 1.08 |
| PEG-b-PPLG | | 10500 | 22224 | 24491 | 25902 | 1.10 |

Figure 4:
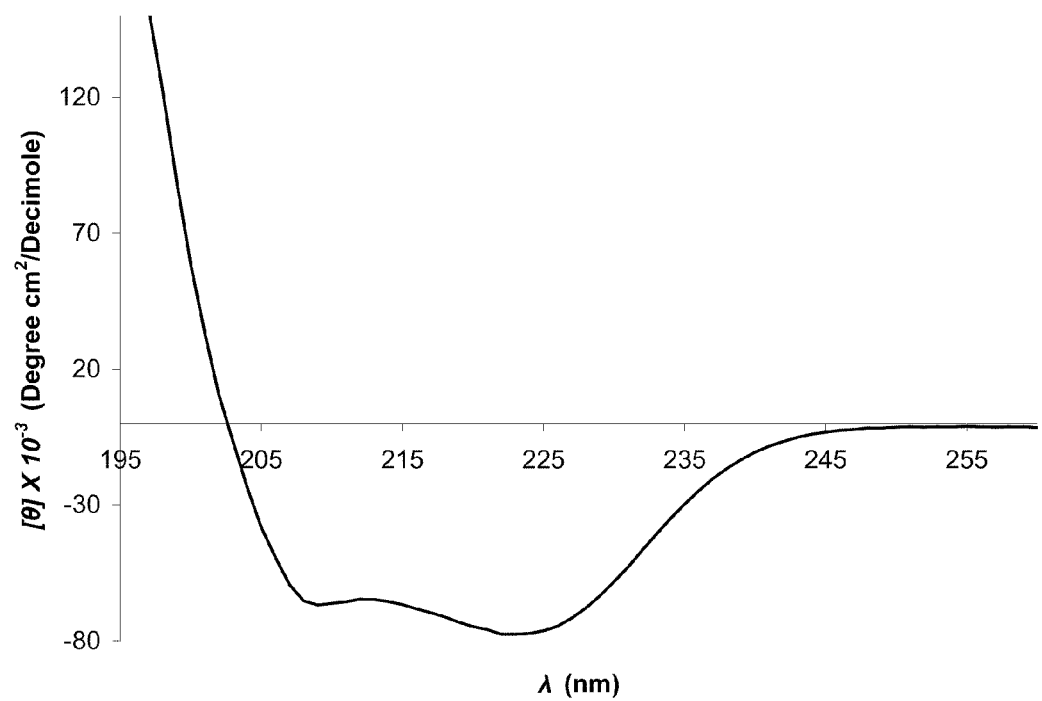
FIG. 4 depicts CD of PEG-b-PPLG in water at a concentration of 1 mg/mL. The minimums at 208 nm and 222 nm indicate that the polymer has an α-helical structure.

The GPC traces show a molecular weight shift indicating the successful addition of the PPLG block. The characteristic CD spectra of an α-helix structure is shown in FIG. 4.

Amine Functionalized Polypeptides Synthesized by "Click Chemistry"

Figure 11:
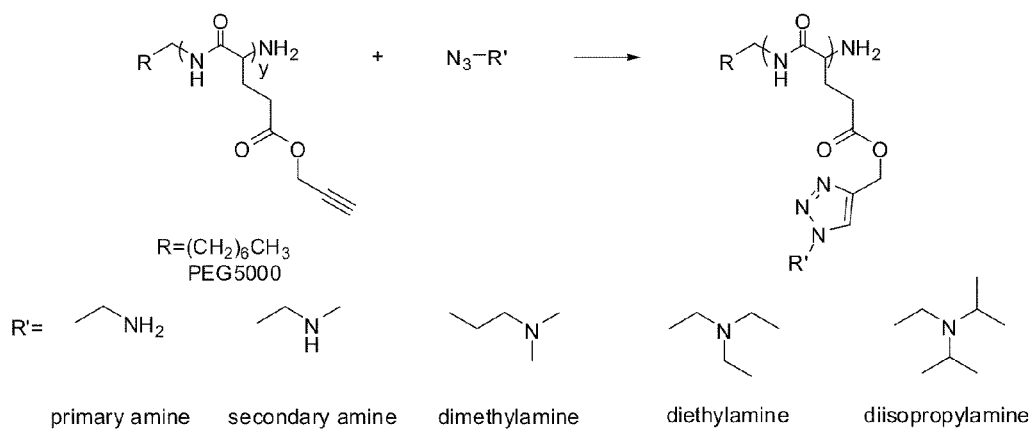
FIG. 11 depicts attachment of various amine groups to PPLG.

A series of amine groups, shown in FIG. 11, was attached to PPLG to demonstrate the incorporation of pH responsive groups for endosomal buffering. The siRNA complexation efficiency of these polymers was determined. The PPLG homopolymer used for the experiments was characterized by $^1$H NMR in DMF-d$_7$ (n=78) and DMF GPC (M$_n$=16,010 g/mol, PDI=1.15).

Figure 12:
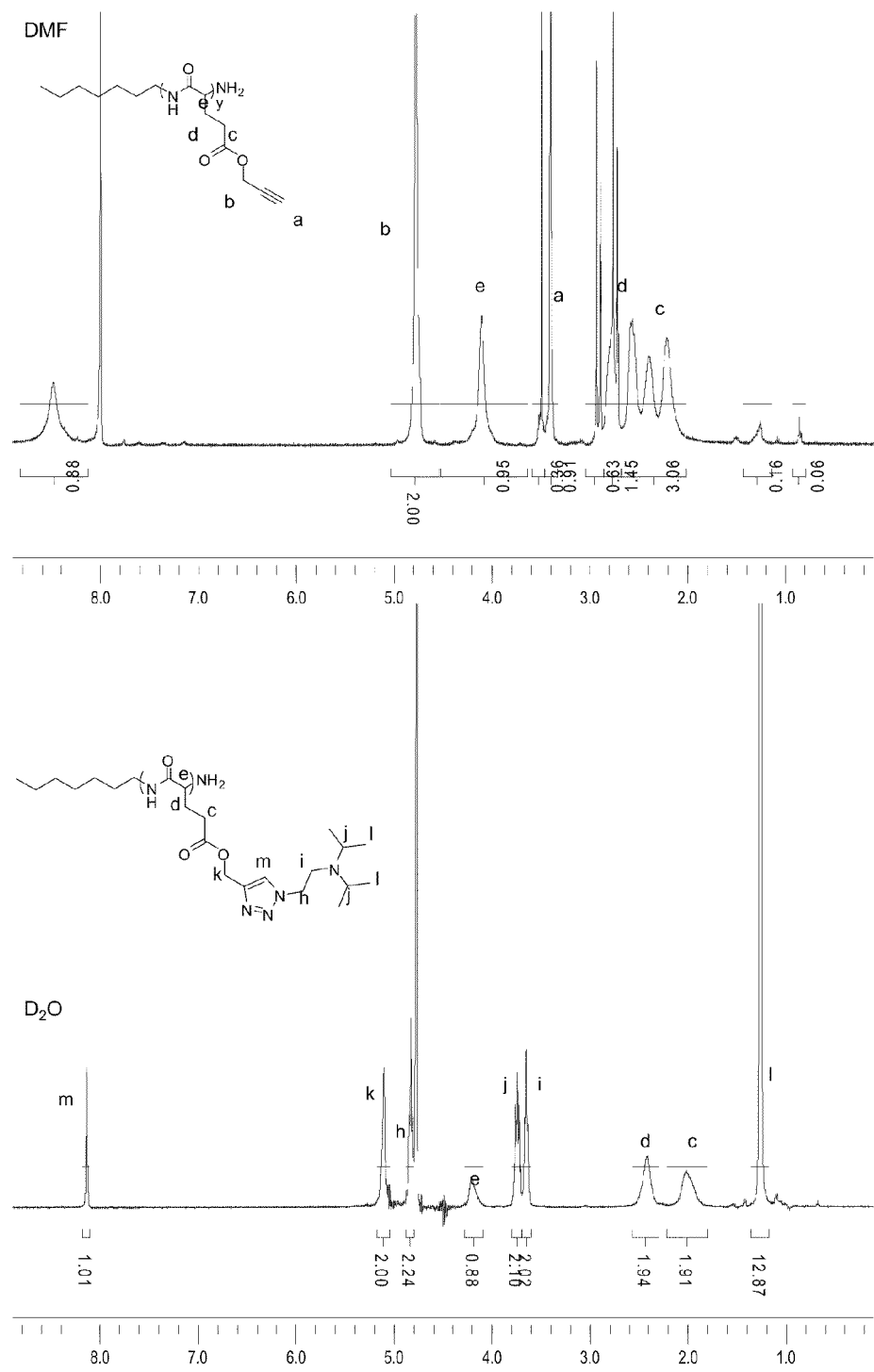
FIG. 12 depicts the NMR of PPLG and PPLG coupled with 2-azidoethyldiisopropylamine.

Functionalization of the Poly(γ-propargyl L-glutamate) with amine groups. The PPLG was coupled with amine-N$_3$ using CuBr/PMDETA as catalyst in DMF with a molar ratio of alkyne/azide/CuBr/PMDETA equal to 1/1.5/0.1/0.1. After the reaction was complete, the reaction solution was placed in a 3500 MW cut off dialysis bag and diluted with an equal part of water by volume. The polymer was purified by dialysis against water acidified with HCl (pH≦5). The polymer structure was confirmed by $^1$H NMR in D$_2$O. For all amines coupled to the PPLG, the efficiency was near 100%. $^1$H NMRs of PPLG and PPLG coupled with 2-Azidoethyldiisopropylamine, shown in FIG. 12.

Figure 13:
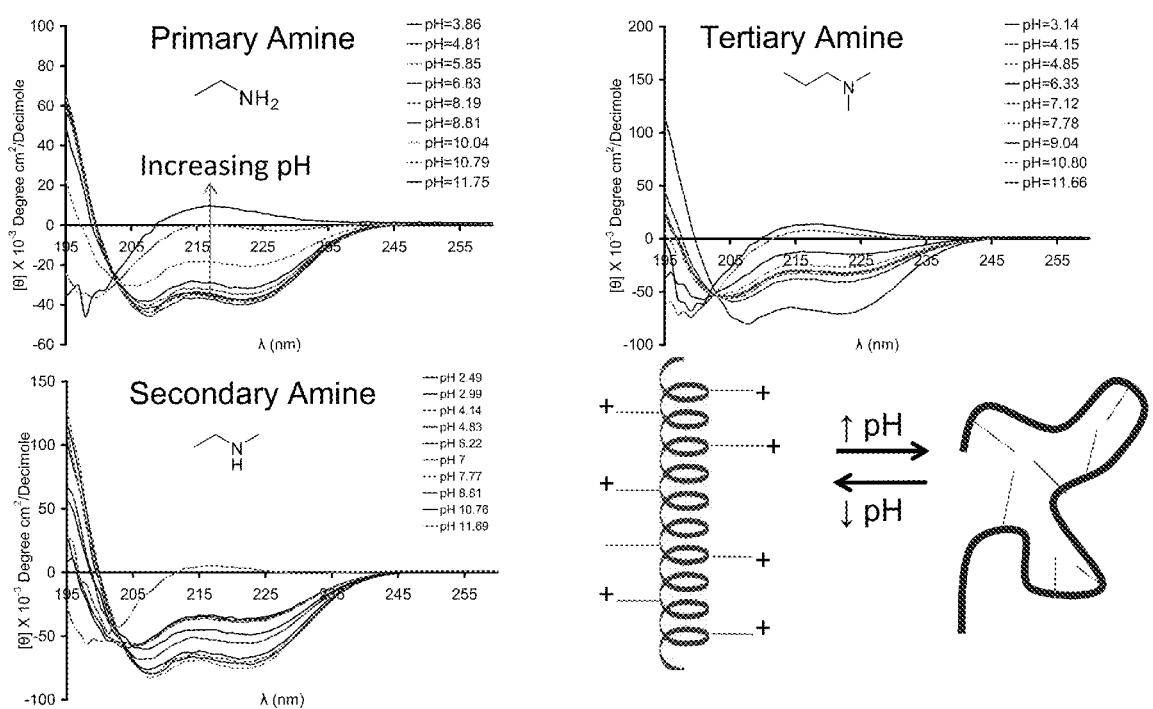
FIG. 13 depicts circular dichroism spectra.

Circular dichroism study. Circular dichroism was used to determine the conformation changes of the various polymers as a function of pH (see FIG. 13). For all polymers tested, the polymer chain adapted an α-helical conformation at a low pH and a random coil conformation at a high pH. Depending on the pKa of the amine side groups, the pH at which the α-helical conformation change occurred varied.

Figure 14:
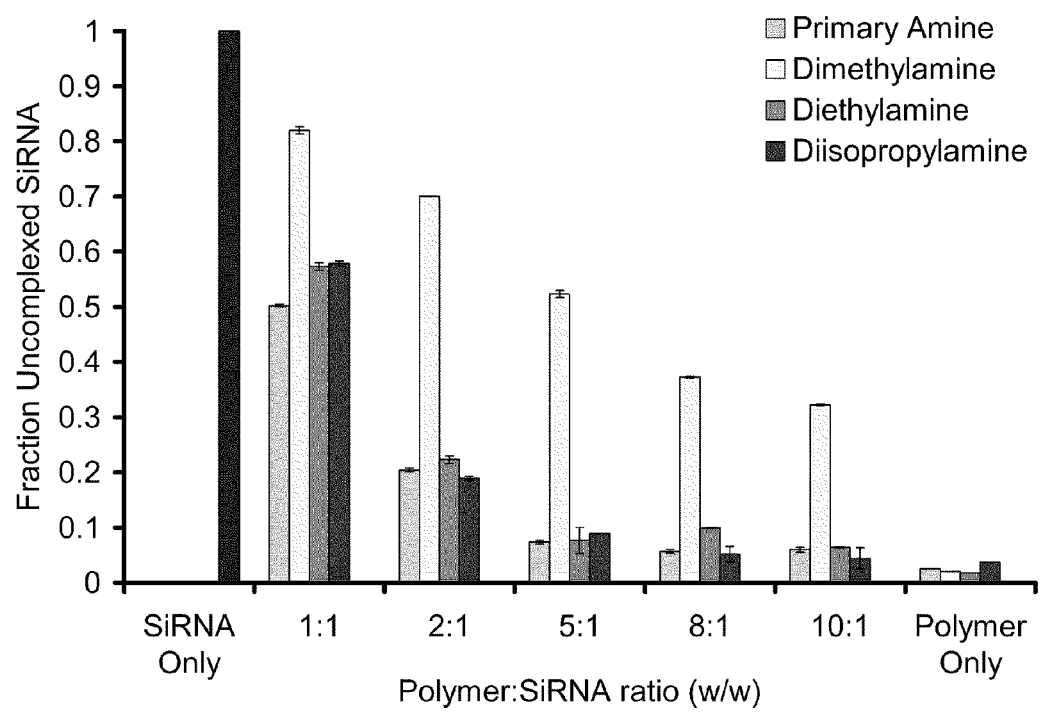
FIG. 14 depicts a graph showing fraction of uncomplexed siRNA for selected amine-containing polymers at various polymer:siRNA ratios (w/w).
Figure 15:
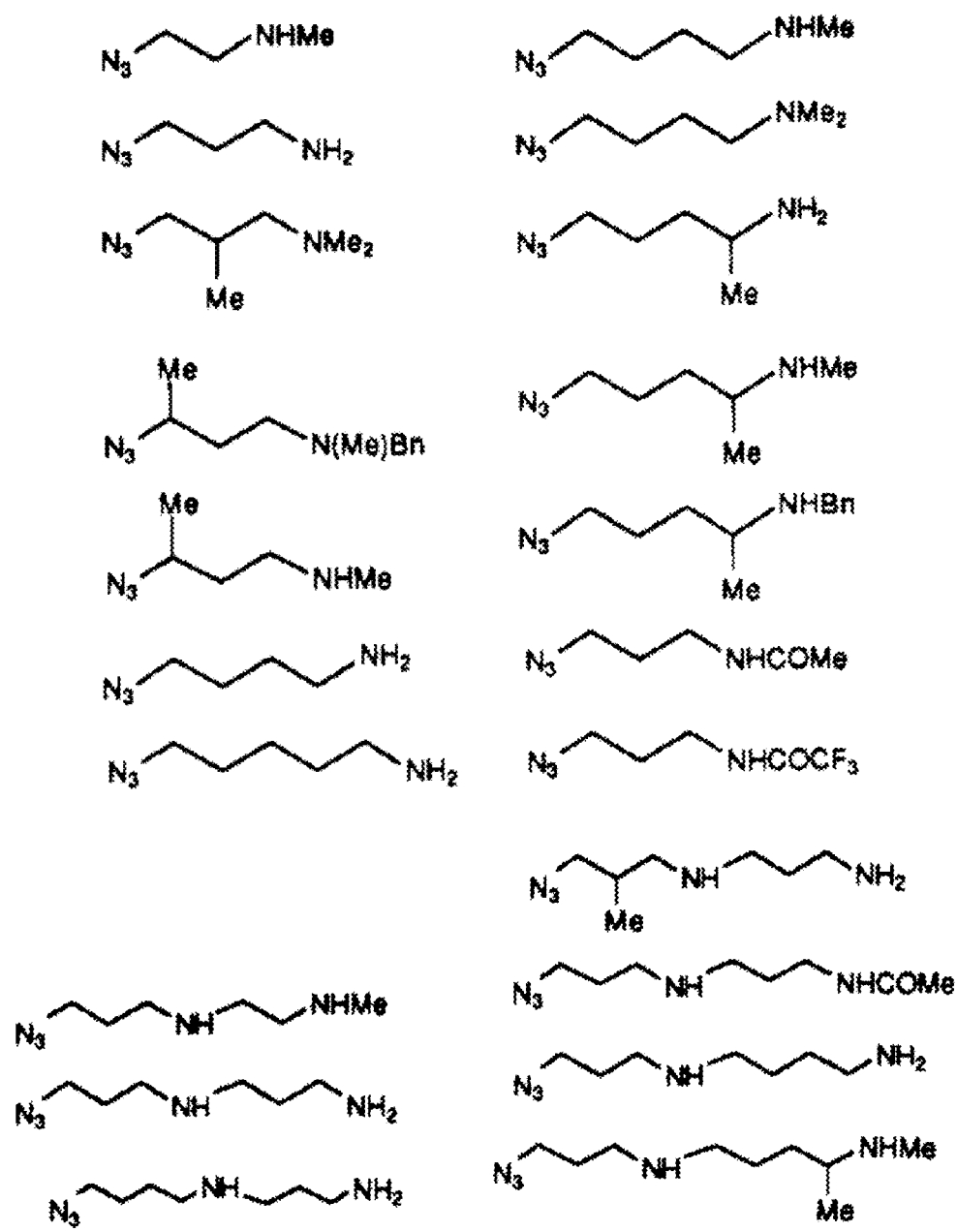
FIG. 15 depicts selected azides, the preparation of which are described in *J. Org. Chem.* 1993, 58, 3736-3741, which is hereby incorporated by reference.

Gene delivery. Studies have been performed to determine if these polymer complex with siRNA. For the complexation studies, polymers were mixed with siRNA at various polymer to siRNA ratios (w/w) ranging from 1:1 to 10:1 in sodium acetate buffer (pH5.5). A Ribogreen assay was used to determine the complexation efficiency of each polymer at the various ratios, shown in FIG. 14. As shown in FIG. 14, all polymers complex with siRNA at varying degrees.

Ribogreen assay for siRNA complexation. A Ribogreen assay (QuantiT Ribogreen RNA Reagent, Invitrogen) was performed to determine the complexation efficiency of the polymers with siRNA. A set concentration of siRNA was placed in each well of a 96 well plate and the appropriate amount of polymer was added to attain the desired polymer:siRNA ratio (w/w). After waiting 10 minutes, a standard amount of Ribogreen was added to each well and the fluorescence of each well was measure. The fraction of uncomplexed siRNA was determined by comparing the fluorescence of the polymer complexes with the fluorescence of a siRNA control.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A polymer comprising a plurality of subunits represented by formula IV:

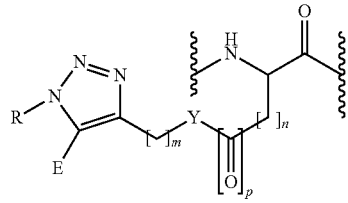

or a tautomer, enantiomer or stereoisomer thereof;
wherein, independently for each occurrence,
E is hydrogen or alkyl;
R is alkyl, haloalkyl, cycloalkyl, (cycloalkyl)alkyl, heterocyclyl, (heterocyclyl)alkyl, aryl, aralkyl, heteroaryl, heteroaralkyl, alkoxy,

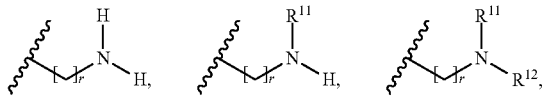

alkyloxycarbonylalkyl, carboxyalkyl, aminocarbonylalkyl, aminoalkyl,

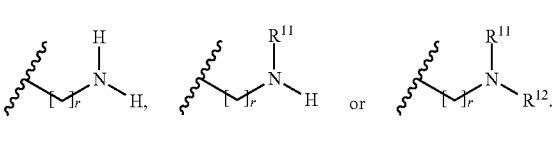

aminoalkylaminoalkyl, a polymer, polystyrene, polyethylene glycol, poly(methyl methyacrylate), a fluorescent dye or a radioactive dye;
d is about 10 to about 300;
W is hydroxy, a protected hydroxy, alkoxy, aryloxy, heteroaryloxy, aralkoxy, heteroaralkoxy, amino or a protected amino;
r is 1-10;
$R^{11}$ is alkyl, aminoalkyl or alkoxycarbonylaminoalkyl;
$R^{12}$ is alkyl, aminoalkyl or alkoxycarbonylaminoalkyl;
m is 1-20 inclusive;
p is 0 or 1;
Y is O, N(H), N(alkyl), C(H)$_2$, C(H)(alkyl) or C(alkyl)$_2$; and
n is 1-10 inclusive.

2. The polymer of claim 1, wherein E is hydrogen.
3. The polymer of claim 1, wherein Y is O.
4. The polymer of claim 1, wherein m is 2; p is 1; and n is 2.
5. The polymer of claim 1, wherein m is 2; p is 1; n is 2; Y is O; and E is hydrogen.
6. The polymer of claim 1, wherein R is

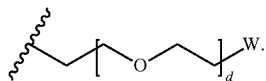

7. The polymer of claim 1, wherein R is

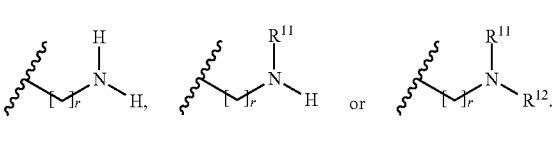

8. A nanoparticle comprising a plurality of polymers of claim 7.
9. The nanoparticle of claim 8, further comprising siRNA.
10. The polymer of claim 1, wherein R is a polymer.
11. The polymer of claim 1, wherein R is polyethylene glycol.

* * * * *